(12) United States Patent
Goldbach et al.

US010646514B2

(10) Patent No.: US 10,646,514 B2
(45) Date of Patent: May 12, 2020

(54) PROCESSING METHODS OF SOLGEL-DERIVED BIOACTIVE GLASS-CERAMIC COMPOSITIONS AND METHODS OF USING THE SAME

(71) Applicant: NOVABONE PRODUCTS, LLC, Alachua, FL (US)

(72) Inventors: Chloë Goldbach, Gainesville, FL (US); Gregory J. Pomrink, Newberry, FL (US); Roy Layne Howell, Gainesville, FL (US); Meryem Demir, Gainesville, FL (US)

(73) Assignee: NOVABONE PRODUCTS, LLC, Alachua, FL (US)

( * ) Notice: Subject to any disclaimer, the term of this patent is extended or adjusted under 35 U.S.C. 154(b) by 8 days.

(21) Appl. No.: 15/478,742

(22) Filed: Apr. 4, 2017

(65) Prior Publication Data

US 2017/0266231 A1    Sep. 21, 2017

Related U.S. Application Data

(60) Continuation-in-part of application No. 15/352,009, filed on Nov. 15, 2016, now Pat. No. 10,143,707, which is a division of application No. 14/312,276, filed on Jun. 23, 2014, now abandoned, which is a continuation-in-part of application No. 14/204,816, filed on Mar. 11, 2014, now Pat. No. 9,498,459.

(60) Provisional application No. 61/782,849, filed on Mar. 14, 2013, provisional application No. 61/786,991, filed on Mar. 15, 2013, provisional application No. 62/318,513, filed on Apr. 5, 2016.

(51) Int. Cl.
| | |
|---|---|
| C03C 10/00 | (2006.01) |
| A61K 8/25 | (2006.01) |
| A61L 27/10 | (2006.01) |
| A61L 27/56 | (2006.01) |
| C03C 4/00 | (2006.01) |
| A61K 33/42 | (2006.01) |
| A61L 27/54 | (2006.01) |
| A61L 26/00 | (2006.01) |
| C03C 3/097 | (2006.01) |
| A61K 33/14 | (2006.01) |
| A61K 33/08 | (2006.01) |
| A61K 33/22 | (2006.01) |
| A61Q 11/00 | (2006.01) |
| C03C 1/00 | (2006.01) |
| A61L 27/52 | (2006.01) |
| C03B 19/12 | (2006.01) |
| C03B 32/02 | (2006.01) |

(52) U.S. Cl.
CPC ........... *A61K 33/42* (2013.01); *A61K 8/25* (2013.01); *A61K 33/08* (2013.01); *A61K 33/14* (2013.01); *A61K 33/22* (2013.01); *A61L 26/0004* (2013.01); *A61L 26/0066* (2013.01); *A61L 26/0085* (2013.01); *A61L 27/10* (2013.01); *A61L 27/52* (2013.01); *A61L 27/54* (2013.01); *A61L 27/56* (2013.01); *A61Q 11/00* (2013.01); *C03B 19/12* (2013.01); *C03B 32/02* (2013.01); *C03C 1/006* (2013.01); *C03C 3/097* (2013.01); *C03C 4/0007* (2013.01); *C03C 10/0009* (2013.01); *A61L 2400/04* (2013.01); *A61L 2430/02* (2013.01); *A61L 2430/34* (2013.01)

(58) Field of Classification Search
None
See application file for complete search history.

(56) References Cited

U.S. PATENT DOCUMENTS

| | | | |
|---|---|---|---|
| 5,074,916 A | 12/1991 | Hench et al. | |
| 5,240,488 A * | 8/1993 | Chandross | C03B 19/12 501/12 |
| 5,558,701 A | 9/1996 | Patel | |
| 6,171,986 B1 | 1/2001 | Zhong | |
| 6,328,990 B1 | 12/2001 | Ducheyne et al. | |
| 6,663,878 B1 * | 12/2003 | Greenspan | A61K 33/42 424/422 |
| 9,498,459 B2 | 11/2016 | Pomrink et al. | |
| 2002/0055143 A1 | 5/2002 | Bell et al. | |
| 2005/0251267 A1 | 11/2005 | Winterbottom et al. | |
| 2007/0245772 A1 | 10/2007 | Lieberman et al. | |
| 2007/0275021 A1 | 11/2007 | Lee et al. | |
| 2009/0186013 A1 | 7/2009 | Stucky et al. | |
| 2009/0208428 A1 | 8/2009 | Hill et al. | |
| 2009/0208923 A1 | 8/2009 | Gelfand et al. | |
| 2009/0232902 A1 | 9/2009 | Liu et al. | |

(Continued)

FOREIGN PATENT DOCUMENTS

| | | | |
|---|---|---|---|
| WO | WO 98/46164 A1 | 10/1998 | |
| WO | WO 2007/017756 A2 | 2/2007 | |
| WO | WO-2007017756 A2 * | 2/2007 | ........... A61L 27/446 |

(Continued)

OTHER PUBLICATIONS

Pons et al., "A new route to aerogels: Monolithic silica cryogels", J Non-Crystalline Solids 358: 461-469 (2012) (Year: 2012).*

(Continued)

*Primary Examiner* — Monica A Shin

(74) *Attorney, Agent, or Firm* — Brinks Gilson & Lione

(57) ABSTRACT

Methods for processing and or removing organic residuals and or impurities from a solgel-derived bioactive glass-ceramic and compositions comprising solgel-derived bioactive glass-ceramics processed using these methods, are described.

12 Claims, 8 Drawing Sheets

(56) References Cited

U.S. PATENT DOCUMENTS

2012/0058250 A1   3/2012  Wu et al.
2014/0017281 A1   1/2014  Pomrink et al.

FOREIGN PATENT DOCUMENTS

| WO | WO 2007/144662 A1 | 12/2007 | |
| WO | WO 2009/013512 A1 | 1/2009 | |
| WO | WO-2009013512 A1 * | 1/2009 | ............. A61L 15/18 |
| WO | WO 2015/137990 A1 | 5/2015 | |

OTHER PUBLICATIONS

International Search Report received in PCT Application No. PCT/US14/22628 dated Jun. 16, 2014.

Cacciotti, et al., "Sol-gel Derived 45S5 Bioglass: Synthesis, Microstructural Evolution and Thermal Behaviour", *J Mater Sci: Mater Med*, 23:1849-66 (2012).

Chen, et al., "A new sol-gel process for producing $Na_2O$-containing bioactive glass ceramics", *Acta Biomaterialia*, V6(10): 4143-53 (2010).

Chen, et al.,"Fabrication and Characterization of Sol-gel Derived 45S5 Bioglass—Ceramic Scaffolds", *Acta Biomaterialia*, 7: 3636-26 (2011).

Siqueira, et al., "Gel-derived $SiO_2$—CaO—$Na_2O$—$P_2O_5$ bioactive powders: Synthesis and in vitro bioactivity", *Materials Science and Engineering*, 31(5): 983-91 (2011).

International Search Report received in PCT Application No. PCT/US14/43638 dated Oct. 15, 2014.

International Preliminary Report and Written Opinion received in PCT Application No. PCT/US2014/022628 dated Sep. 15, 2014.

International Preliminary Report and Written Opinion received in PCT Application No. PCT/US2014/043638 dated Sep. 22, 2016.

Carta et al., "Sol-gel synthesis of the P2O5—CaO—Na2O—SiO2 system as a novel bioresorbable glass," *J Mater Chem*, 15:2134-2140 (2005).

El-Ghannam, "Advanced bioceramics composite for bone tissue engineering: design principles and structure-bioactivity relationship," *J Biomed Mater Res*, 69A:490-501 (2004).

European reporting letter dated Jan. 6, 2017, European Search report dated Dec. 8, 2016 and communication dated Jan. 3, 2017 received in European Patent Application No. 14768673.7-1354/2969984.

Adams et al., "Sol-Gel Synthesis of $SiO_2$—CaO—$Na_2O$—$P_2O_5$ Bioactive Glass Ceramic from Sodium Metasilicate," *New Journal of Glass and Ceramics*, 3:11-15 (2013).

Ostomel et al., "Spherical Bioactive Glass with Enhanced Rates of Hydroxyapatite Deposition and Hemostatic Activity," *Bioactive Glasses*, 2(11):1261-1265 (2006).

International Search Report and The Written Opinion of the International Searching Authority, or the Declaration received in PCT Application No. PCT/US17/25906 dated Jul. 3, 2017.

Danks et al., "The evolution of 'sol-gel' chemistry as a technique for materials synthesis," *Materials Horizons*, 3:91-112 (Dec. 15, 2015).

Wikipedia, *Bioglass*, https://en.wikipedia.org/wiki/Bioglass pp. 1-6, downloaded Jun. 3, 2017.

Bahniuk et al., "Bioactive Glass 45S5 Powders: Effect of Synthesis Route and Resultant Surface Chemistry and Crystallinity on Protein Adsorption from Human Plasma," *Biointerphases*, 7:41 (2012).

First Office Action received in European Patent Application No. 11 751 335.8-1452 dated Oct. 10, 2017.

Reporting letter received from European Associate in European Patent Application No. 11 751 335.8-1452 dated Oct. 24, 2017.

Reporting letter received from European associate dated Sep. 26, 2017, and Supplementary European Search Report dated Sep. 25, 2017 received in European Patent Application No. 14885246.0-1466/3116836.

Reporting letter received from Australian associate dated Feb. 1, 2018, and Examination Report No. 1 received in Australian Application No. 2014386243 dated Jan. 25, 2018.

Notification Concerning Transmittal of the International Preliminary Report on Patentability dated Oct. 18, 2018 and International Preliminary Report on Patentability dated Oct. 9, 2018(*) for PCT/US2017/025906.

* cited by examiner

PROCESSING METHODS OF SOLGEL-DERIVED BIOACTIVE GLASS-CERAMIC COMPOSITIONS AND METHODS OF USING THE SAME

CROSS-REFERENCE TO RELATED APPLICATIONS

This application claims the benefit of U.S. Provisional Patent Application No. 62/318,513, filed Apr. 5, 2016, and is a continuation-in-part application of U.S. patent application Ser. No. 15/352,009, filed Nov. 15, 2016, which is a divisional application of U.S. patent application Ser. No. 14/312,276, filed Jun. 23, 2014, which is a continuation-in-part application of U.S. patent application Ser. No. 14/204,816, filed Mar. 11, 2014, issued as U.S. Pat. No. 9,498,459 on Nov. 22, 2016, which claims the benefit of U.S. Provisional Patent Application No. 61/782,849, filed Mar. 14, 2013 and claims benefit of U.S. Provisional Application No. 61/786,991, filed Mar. 15, 2013, the entire contents of which are hereby incorporated herein by reference.

BACKGROUND

Bioactive glass-ceramics are compositions that are capable of inducing specific biological activity. Specifically, bioactive glass-ceramics are widely used bone repair materials due to their unique properties, such as osteoconductivity, osteoinductivity and biodegradability.

In early 1970s, Larry L. Hench reported on the bone bonding ability observed for the glass-ceramic system based on $SiO_2$—$CaO$—$Na_2O$—$P_2O_5$ which was given the trade name Bioglass® (Hench L L, et al., Bonding mechanisms at the interface of ceramic prosthetic materials. *J Biomed Mater Res.*, 5:117-41 (1971)). Today a wide range of bioactive glass compositions have been developed through different synthesis routes and found a variety of applications including soft tissue bonding (Hench L L. Bioceramics. *J Am Ceram Soc.*, 81:1705-28 (1998); Wilson J, Nicolletti D. Bonding of soft tissues to bioglass. In: Yamamuro T, Hench L L, Wilson J, ed. Handbook of bioactive ceramics: bioactive glasses and glass ceramics. Boca Raton Fla.:CRC Press, 283-302 (1990); and Wilson J, et al. Toxicology and biocompatibility of bioglasses. *J Biomed Mater Res.*, 15:805-17 (1981)), lung tissue engineering (Tan A, et al. The effect of 58S bioactive solgel-derived foams on the growth of murine lung epithelial cells. *Key Eng Mater.*, 240-242:719-24 (2003); and Verrier S, et al. PDLLA/Bioglass composites for soft-tissue and hard-tissue engineering: an in vitro cell biology assessment. *Biomaterials.* 25:3013-21 (2004)), inducing angiogenesis (Day R M. Bioactive glass stimulates the secretion of angiogenic growth factors and angiogenesis in vitro. *Tissue Eng.* 11:768-77 (2005)), stimulating the gene expression (Xynos I D, et al. Gene-expression profiling of human osteoblasts following treatment with the ionic products of Bioglass 45S5 dissolution. *J Biomed Mater Res.* 55:151-7 (2001)), and growth factor production in osteoblasts (Xynos I D, et al. Ionic dissolution products of bioactive glass increase proliferation of human osteoblasts and induce insulin like growth factor II mRNA expression and protein synthesis. *Biochem Biophys Res Commun.*, 276:461-5 (2000)), etc.

Bioactive glass-ceramics can be synthesized by melt or solgel methods. The solgel method is a chemical synthesis technique that involves the conversion of a sol, which is a suspension of very small, colloidal particles to a three dimensional interconnected network termed gel. Six steps are usually involved in the preparation of bioactive glass-ceramics by this method. The first step involves the mixing of precursors, which form a low viscosity sol whose viscosity steadily increases as the network interconnect develops. Before the completion of the network formation, the sol is cast into a mold where gelation occurs as the third step.

The resulting three dimensional gel networks are completely filled with pore liquid. Aging is the fourth step, which involves holding the gel in its pore liquid for several hours. In step five, the gel is dried during which the pore liquid and the physically adsorbed water are completely eliminated from the pores. This involves heating at controlled rates at temperatures of 120-180° C.

Chemical stabilization of the gel, often called "calcination" is the sixth step that is necessary to remove the residual components and unwanted byproducts associated with the hydrolysis and condensation reactions. This stabilization step confers to the environmental stability and bioactivity. This step usually is a thermal treatment in the range of 500–900° C., which desorbs surface silanols (Si—OH) and eliminates other residuals from the gel. Usually temperature of calcination for bioactive glass-ceramics is selected to be 600° C. and it is quoted that maximum bioactivity is obtained with minimum stabilization temperature (Xynos I D, et al., Gene-expression profiling of human osteoblasts following treatment with the ionic products of Bioglass 45S5 dissolution. *J Biomed Mater Res.*, 55:151-7 (2001); Xynos I D, et al., Ionic dissolution products of bioactive glass increase proliferation of human osteoblasts and induce insulin like growth factor II mRNA expression and protein synthesis. *Biochem Biophys Res Commun.* 276:461-5 (2000); and Jones J R, et al., Optimising bioactive glass scaffolds for bone tissue engineering. *Biomaterials*, 27:964-73 (2006)). According to Hench et al., calcination also has its effect on increasing the strength and hardness of the gels and converts the network to a glass with network properties similar to the conventional melt derived glasses (Hench L L, Wilson J. An introduction to bioceramics. In: Hench L L, Wilson, ed. Advanced series in ceramics, *USA:World Scientific Publishing Co*, 1-24 (1993).

Since the stabilization of the glass-ceramics (especially sodium based compositions) by conventional heat treatment alter the glass-ceramic properties like particle size, density, surface area, etc., similar to melt derived materials, stabilization of solgel derived structure of these glass-ceramics by another means would be advantageous in this respect. Additionally, these properties are significant in the field of composites as well, where the bioactive glass-ceramics serve as reinforcement in low elastic modulus polymeric matrix. Moreover, it is well reported that the textural features like particle size distribution, specific surface area, porosity, solubility, etc. have a strong influence on bioactivity. This is for the reason that, during the bone bonding mechanism the rate of formation of hydroxyl carbonate apatite (HCA) layer, the interfacial layer that is structurally and chemically equivalent to the mineral phase of the bone, is influenced with the particle size range and powder volume fraction.

Other approaches to stabilization of bioactive glass and to removing impurities have been studied and use ethanol washing (Mukundan L., et al. A new synthesis route to high surface area solgel bioactive glass through alcohol washing. 3(2) (2013))

A new approach to the processing of solgel derived glass-ceramics wherein the glass-ceramics are not subjected to the high temperature chemical stabilization process or solvent washing is described. Hence the current work presents an alternative method of preparing, stabilizing and maintaining the pore structure of the solgel-derived bioactive glass-ceramics.

SUMMARY

Described is bioactive glass-ceramic (e.g., sodium containing) prepared by a solgel process and treated by a novel method that involves at least one of extended low temperature heat treatment, ultraviolet (UV) light treatment, a supercritical carbon dioxide ($scCO_2$) treatment, treatment with oxidizers, freeze drying or lyophilization, or a combination of the treatments, instead of the conventional calcinations process or solvent washing. The described treatment methods remove organic residues or other impurities from the solgel-derived bioactive glass-ceramic resulting in superior compositions for use in medical applications, such as hemostasis and soft tissue repair.

The studies described below proved that the removal of organic residues was achieved with the retention of its inherent bioactive potential while providing the pore structure and surface area of a traditional sodium or potassium free bioactive glass-ceramic (e.g., 58S). The surface area of the glass-ceramic powder was maintained as a result of at least extended low temperature heat treatment process (rapid or stepwise), UV treatment, exposure to an oxidizing environment and/or extraction with supercritical carbon dioxide which add up to the success of the described method(s).

Certain embodiments relate to a method for preparing a solgel-derived bioactive glass-ceramic comprising applying to the solgel-derived bioactive glass-ceramic at least one treatment selected from: (i) an extended low temperature heat treatment comprising rapidly heating the solgel-derived bioactive glass-ceramic to a treatment temperature below about 550° C. and holding the treatment temperature for the reminder of a heat treatment period; (ii) an extended stepwise low temperature heat treatment comprising stepwise heating the solgel-derived bioactive glass-ceramic to at least first treatment temperature at or below about 550° C.; (iii) an ultraviolet (UV) light treatment; (iv) a supercritical carbon dioxide ($scCO_2$) treatment; (v) freeze drying or lyophilization; or (vi) oxidizers to the solgel-derived bioactive glass-ceramic, wherein the at least one treatment results in the removal of at least 5% of organic residuals and or impurities from the solgel-derived bioactive glass-ceramic, wherein the at least one treatment does not affect the pore structure of the solgel-derived bioactive glass-ceramic, and wherein a combination of treatments results in a synergistic removal of organic residuals and or impurities from the solgel-derived bioactive glass-ceramic.

Further embodiments relate to a method for removing organic residuals and or impurities from a solgel-derived bioactive glass-ceramic comprising applying to the solgel-derived bioactive glass-ceramic at least one treatment selected from: (i) an extended low temperature heat treatment comprising rapidly heating the solgel-derived bioactive glass-ceramic to a treatment temperature below 550° C. and holding the treatment temperature for the reminder of a heat treatment period; (ii) an extended low temperature stepwise heat treatment comprising stepwise heating the solgel-derived bioactive glass-ceramic to at least first treatment temperature at or below about 500° C.; (iii) an ultraviolet (UV) light treatment; (iv) a supercritical carbon dioxide ($scCO_2$) treatment; (v) freeze drying or lyophilization; or (vi) oxidizers to the solgel-derived bioactive glass-ceramic, wherein at least one treatment results in the removal of at least 5% and up to 100% of organic residuals and or impurities from the solgel-derived bioactive glass-ceramic, wherein at least one treatment does not affect the pore structure of the solgel-derived bioactive glass-ceramic, and wherein a combination of treatments results in a synergistic removal of organic residuals and or impurities from the solgel-derived bioactive glass-ceramic.

In the described methods, the solgel-derived bioactive glass-ceramic is sodium-based solgel-derived bioactive glass-ceramic.

Certain other embodiments relate to a soft tissue repair composition comprising the solgel-derived bioactive glass-ceramic prepared according to the described method. The solgel-derived bioactive glass-ceramic may be in the form of a particle, sphere, fiber, mesh, sheet or a combination of these forms. The size of the bioactive glass-ceramic particle may be in a range from about 0.01 μm to about 5 mm. The composition may be used to form a synthetic bone-grafting putty, paste, gel, strip or waxy solid. The osteoconductive composition promotes osteoblast activity upon introduction into a bony defect. The composition may be used in treating a variety orthopedic indications including spine, cranial maxillofacial and extremity reconstruction. The composition may also be used for hemostasis and or the regeneration of soft tissues.

Yet certain other embodiments relate to a bone repair composition comprising the solgel-derived bioactive glass-ceramic prepared according to the described method. The solgel-derived bioactive glass-ceramic may be in the form of a particle, sphere, fiber, mesh, sheet or a combination of these forms. The size of the bioactive glass-ceramic particle may be in a range from about 0.01 μm to about 5 mm. The composition may be used to form a synthetic bone-grafting putty, paste, gel, strip or waxy solid. The composition promotes osteointegration upon introduction into a bony defect. The composition may be for treating a bone defect or a bone gap. The composition may be for regeneration of hard tissues.

Certain other embodiments relate to a method for treating a bone having a bone gap or a bone defect comprising contacting the bone at or near the site of the bone defect with the described bone repair composition.

DETAILED DESCRIPTION OF THE DRAWINGS AND THE PRESENTLY PREFERRED EMBODIMENTS

Figure 1:
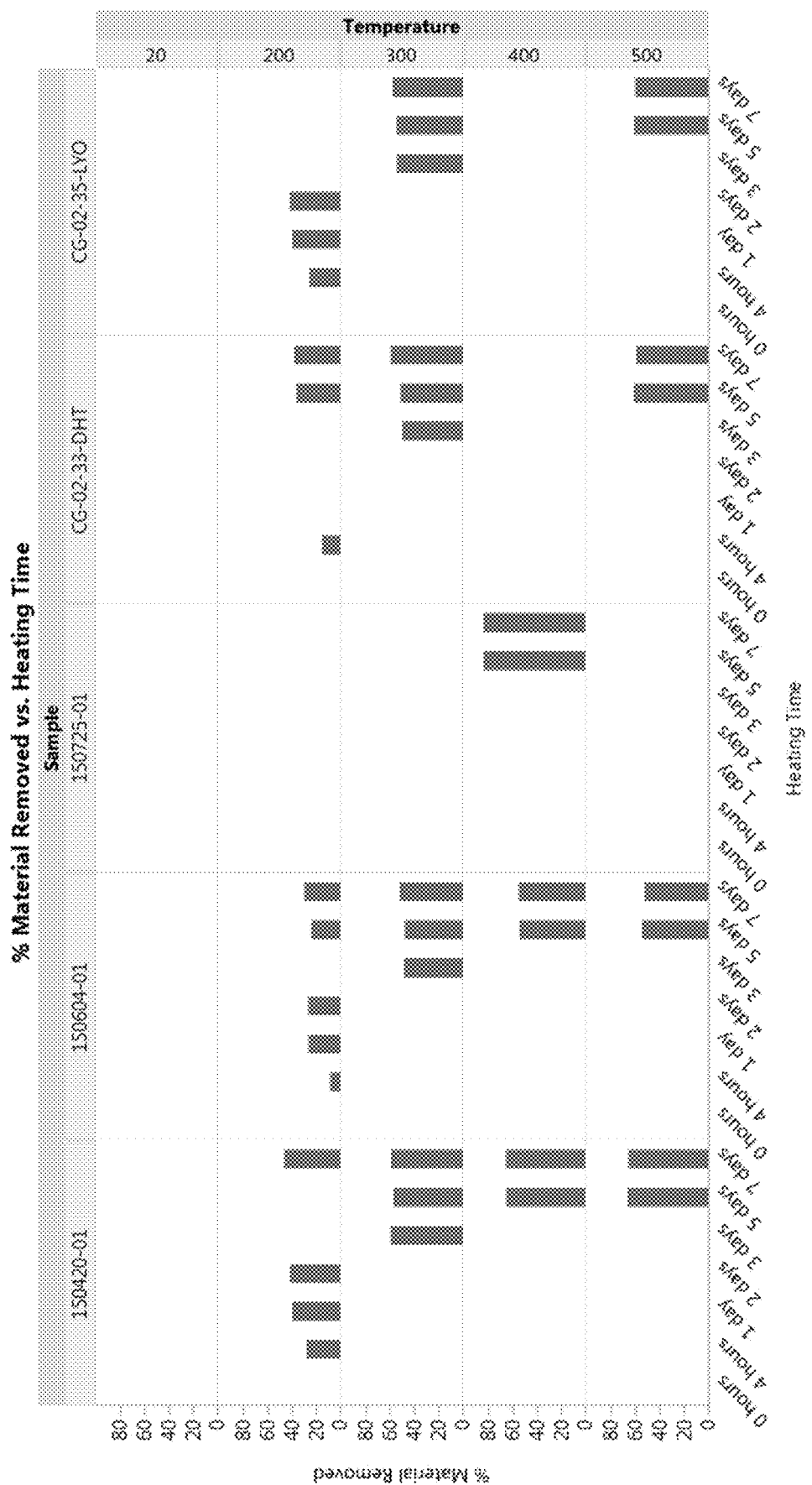
FIG. 1 displays a bar chart comparison of the percentage of material removed from each tested solgel-derived bioactive glass-ceramic sample based upon temperatures and heating times. Note that 20° C. refers to samples that remained at ambient temperature and were not subjected to heat treatment.

As discussed in the background section, the traditional "calcination" step necessary to remove the residual components and unwanted byproducts associated with the hydrolysis and condensation reactions is a rapid (less than 30 minutes) thermal treatment in the range of 550-900° C. Besides reducing the melting temperature for glass-ceramic preparation by the traditional route, the addition of Na into bioactive glass-ceramic materials makes them more soluble in aqueous media. However, rapid heating a solgel glass-ceramic containing significant amounts of sodium or potassium at or above 550° C. has been shown to result in a subsequent collapse of the solgel glass-ceramic pore structure. Therefore, traditional methods do not allow for preparing a high sodium or potassium containing sol-gel glass-ceramic with a high surface area (1.5-200 times greater than the melt derived process) using the traditional sol-gel method since the calcination step (i.e., rapid heating at or above 550° C.) causes the solgel glass-ceramic structure to collapse yielding a surface area similar to melt derived compositions (see, e.g. Table 2 below) Surprisingly, Applicants have shown that high surface areas can be obtained when applying slow (e.g., 24 to 72 hour heat ramp), stepwise heating up to about 550° C. rather than rapid heating at 550-900° C. (Table 5).

The present study confirms that the new processing routes of solgel-derived glass-ceramics through extended low temperature (i.e., a temperature ≤550° C.) heat treatments (e.g., rapid and or stepwise), ultraviolet (UV) light treatment, a supercritical carbon dioxide ($scCO_2$) treatment, treatment with oxidizers, freeze drying or lyophilization, or a combination of the treatments offer an alternate and superior way of preparation, stabilization and maintaining the pore structure of alkali metal containing bioactive glass-ceramics as compared to the conventional preparation methods. Importantly, the new processing methods result in solgel-derived bioactive glass-ceramic that is substantially free from organic residuals and or impurities, while maintaining the desired properties of the solgel-derived bioactive glass-ceramic, such as particle size distribution, specific surface area, porosity, etc.

Sodium containing solgel-derived glass-ceramics have a lower melting point, typically, experiencing pore structure collapse at temperatures higher than 550° C. Because of this, solgel 45S5 glass-ceramics have historically had low surface areas (0.1 to <12 m²/g) while 58S solgel-derived glass-ceramics typically have a surface area higher than 100 m²/g. As described in detail in the examples, a variety of new solgel-derived 45S and 45S5 solutions were prepared and subjected to low temperature heat treatments (<550° C.) for extended periods of time, ultraviolet light, supercritical carbon dioxide ($scCO_2$) and/or treatment with oxidizers to assess the removal of organic residuals and impurities and resulting specific surface areas. All treatments resulted in removal of organic residuals and or impurities, while maintaining the desired properties of the solgel-derived bioactive glass-ceramic, such as particle size distribution, specific surface area, porosity, etc. Surprisingly, when more than one of the treatments were used in combination, the combination of treatments resulted in a synergistic removal of organic residuals and or impurities from the solgel-derived bioactive glass-ceramic.

Bioactive glass-ceramic prepared or stabilized by the described methods or a combination of methods was found to be superior as compared to the bioactive glass-ceramic sample conventionally processed. For example, the percentage of organic residuals or impurities removal increased with increasing temperature (up to 600° C.) and treatment times, where heating to 400° C. resulted in the highest percentage of organic residuals or impurities removal, while maintaining the pore structure of the solgel-derived bioactive glass-ceramic and increasing the specific surface area as compared to conventionally treated solgel-derived bioactive glass-ceramic. The specific surface area increased from 4 to over 10 times with a value for the surface area as high as 143.9 m²/g being achieved (e.g., for samples treated with 16 hours of UV followed by 36 hours of stepwise heating to 400° C.). Importantly, the effect of the extended low temperature heat treatment was determined to be only physical, reducing the density of the material. Moreover, it is believed that the solgel-derived bioactive glass-ceramic samples processed by the described treatment methods or a combination of treatment methods improve the osteoconductive, osteostimulative, and bioactive properties. Hence the results confirm that the stabilization has been achieved with an increase of surface area by the described methods of extended low temperature heat treatments, ultraviolet (UV) light treatment, a supercritical carbon dioxide ($scCO_2$) treatment, treatment with oxidizers, freeze drying or lyophilization, or a combination of the treatments, and are recommended to improve the biomimmicity of various scaffolds used for soft and hard tissue engineering applications.

The bioactive solgels processed in accordance with the described methods of extended low temperature heat treatments, ultraviolet (UV) light treatment, a supercritical carbon dioxide ($scCO_2$) treatment, treatment with oxidizers, or a combination of the treatments provide for solgel-derived bioactive glass-ceramic compositions, which are substantially free from organic residuals and or impurities and have significantly improved hemostatic properties as compared to melt-derived 45S5 Bioglass-ceramic and or other solgel compositions prepared by conventional methods. In addition, it is expected that bioactive solgels processed through the extended low temperature heat treatments, ultraviolet (UV) light treatment, a supercritical carbon dioxide ($scCO_2$) treatment, treatment with oxidizers, freeze drying or lyophilization, or a combination of the treatments will exhibit equivalent or better hemostatic properties as compared to some current commercially available hemostasis products.

As used herein and in the appended claims, the singular forms "a," "and," and "the" include plural referents unless the context clearly dictates otherwise. Thus, for example, reference to "a protein" includes a plurality of such proteins and reference to "the progenitor cell" includes reference to one or more progenitor cells known to those skilled in the art, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, compositions, devices and materials are described herein.

The term "organic residuals and or impurities" or "organics" may be used interchangeably and refer to residual components and unwanted byproducts associated with the hydrolysis and condensation reactions during the process of preparing solgel-derived bioactive glass-ceramic. For example, organic residuals may be molecules classified as any carboxylic acid, alcohol, aldehyde, alkane, alkene, alkyne, amine, amide, aromatic ring, ester, ether, imide or molecules containing one or more functional groups and any derivatives thereof along with any of the anions of the respective sodium, calcium or other metal salts (especially alkali, alkali earth, transition and post transition metals) depending upon the intended final composition of the glass-ceramic. In addition, any hydrocarbon based cations and ligands of organosilicates, organosilanes and organophosphates would be sources of organics that could be removed through the described processes. Other materials like cations and ligands of organoborates, organotitanates or organozirconates are also included, depending upon the intended final composition. Inorganic species like borates, carbonates, halides, phosphates, nitrates, oxides, selenates and sulfates will not be removed with the exception of water, ammonia, ammonium hydroxide and HCl. The non-volatile inorganic species will remain within the structure of the glass ceramic under the described processing conditions.

As discussed in the background section, chemical stabilization of the gel, often called calcination is the final step, which is necessary to remove the residual components and unwanted byproducts associated with the hydrolysis and condensation reactions. This step in conventional methods usually is a thermal treatment in the range of 550-900° C., which desorbs surface silanols (Si—OH) and eliminates other residuals from the gel. Usually temperature of calcination for bioactive glass-ceramics is selected to be 600° C. and it is quoted that maximum bioactivity is obtained with minimum stabilization temperature.

Described herein are alternative process of calcination of solgel-derived bioactive glass-ceramics necessary to remove the organic residual components and unwanted byproducts (e.g., organic residuals and or impurities), while maintaining porosity and increasing the specific surface area of the bioactive glass-ceramic, especially solgel-derived bioactive glass-ceramics containing alkali metal oxides.

As such, certain embodiments relate to a method for removal of organic residuals and/or impurities from a solgel-derived bioactive glass-ceramic. The method includes applying at least one treatment selected from (i) applying an extended low temperature heat treatment to the solgel-derived bioactive glass-ceramic comprising rapidly heating the solgel-derived bioactive glass-ceramic to a treatment temperature below about 550° C. and holding the treatment temperature for the reminder of a heat treatment period; (ii) applying an extended low temperature stepwise heat treatment to the solgel-derived bioactive glass-ceramic comprising stepwise heating the solgel-derived bioactive glass-ceramic to at least first treatment temperature at or below about 550° C.; (iii) applying ultraviolet (UV) light treatment to the solgel-derived bioactive glass-ceramic; (iv) applying a supercritical carbon dioxide ($scCO_2$) treatment to the solgel-derived bioactive glass-ceramic; (v) freeze drying or lyophilization; or (vi) applying oxidizers to the solgel-derived bioactive glass-ceramic. A combination of the treatments may be used to obtain a synergistic removal of organic residuals and/or impurities from a solgel-derived bioactive glass-ceramic. Specifically, the individual treatments or a combination of the listed treatments is contemplated and result in the removal of at least about 0.1% and up to about 100% of organic residuals and or impurities from the solgel-derived bioactive glass-ceramic, where the individual treatments or a combination of the listed treatments does not affect the pore structure of the solgel-derived bioactive glass-ceramic. In certain embodiments, when a combination of treatments is applied to the solgel-derived bioactive glass-ceramic, the combination of treatments can result in a synergistic removal of organic residuals and or impurities from the solgel-derived bioactive glass-ceramic.

The described treatment(s) can result in the removal of about 0.1-100% of organic residuals and or impurities from the solgel-derived bioactive glass-ceramic over a prescribed time period. In certain alternative embodiments, the individual treatments or a combination of treatments can result in the removal of at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, and/or 99.99% of organic residuals and or impurities from the solgel-derived bioactive glass-ceramic over a prescribed time period. In certain embodiments, 100% of the organic residuals and/or impurities can be removed from a solgel-derived bioactive glass-ceramic. It is understood that any percentages in-between the listed percentages are also included.

In certain embodiments, the treatment(s) of a solgel-derived bioactive glass-ceramic with at least one of extended low temperature heat treatment (rapid and or stepwise, as described below), ultraviolet (UV) light treatment, a supercritical carbon dioxide ($scCO_2$) treatment, treatment with oxidizers, freeze drying or lyophilization, or a combination of the treatments can result in a solgel-derived bioactive glass-ceramic that is substantially free of any organic residuals and/or impurities, while maintaining the desired properties of the solgel-derived bioactive glass-ceramic, such as particle size distribution, specific surface area, porosity, etc. The term "substantially free" in reference to a sol-gel derived bioactive glass-ceramic, means that at least 90% of organic residuals and or impurities have been removed from the solgel-derived bioactive glass-ceramic (as compared to untreated on conventionally treated solgel-derived bioactive glass-ceramic) as a result of at least one of extended low temperature heat treatment (rapid and or stepwise), ultraviolet (UV) light treatment, a supercritical carbon dioxide ($scCO_2$) treatment, treatment with oxidizers, freeze drying or lyophilization, or a combination of the treatments.

Certain embodiments relate to a method for removal of organic residuals and/or impurities from a solgel-derived bioactive glass-ceramic. The method includes applying a low temperature heat treatment to the solgel-derived bioactive glass-ceramic for a prescribed time period (i.e., "a heat treatment period"), wherein the "low temperature heat treatment" means that a treatment temperature is below 550° C. In certain embodiments, such as with a stepwise low temperature heat treatment, the treatment temperature may be at or below 550° C., but will not exceed 550° C.

In certain embodiments, the extended low temperature heat treatment(s) may start at a room temperature (about 25° C.; "a starting temperature") and continue to increase stepwise to a temperature (i.e., "a treatment temperature") of about 105° C., 200° C., 300° C., 400° C., and or 500° C., or a combination thereof (i.e., "a first treatment temperature," followed by "a second treatment temperature," followed by "a third treatment temperature," etc.), or temperatures between the listed temperatures (e.g., 350° C.) without exceeding a temperature of about 500° C., for a prescribed heat treatment period.

In certain alternative embodiments, the extended low temperature heat treatment may start at a room temperature (about 25° C.) and then rapidly increase to a temperature (i.e., "a treatment temperature") of about 100° C., about 200° C., about 300° C., and/or about 400° C., or higher, or a combination thereof, without reaching a temperature of 500° C. (i.e., the temperature remains below 500° C.), for a prescribed heat treatment period. The terms "rapid heating," "rapidly heating," "rapidly increase" or "rapidly increasing" refer to a time period where upon application of the heat treatment, the temperature reaches a treatment temperature in equal or less than about 30 min (i.e., within minutes/as fast as the oven will heat).

The treatment of a solgel-derived bioactive glass-ceramic with at least one of extended low temperature heat treatment (rapid and or stepwise, as described below), ultraviolet (UV) light treatment, a supercritical carbon dioxide ($scCO_2$) treatment, treatment with oxidizers, or a combination of the treatments may be for "a heat treatment period" or "a prescribed period of time," such as anywhere from about 5 minutes to 7 days or longer. In certain embodiments, the treatment or a combination of treatments may be over 5 to 7 day time period. However, longer time periods are also contemplated (e.g., 8 days, 9 days, and 10 days).

In certain embodiments, the extended low temperature heating will include ramping up (rapidly or slowly (i.e., longer than about 30 min) to a treatment temperature before reaching a plateau. The heating profiles may include, e.g., the following heating profiles:

heating rapidly (within minutes/as fast as the oven will heat) to temperatures between 105 and 400° C.;
20 hour ramp from 25° C. to 300° C., 4 hour hold at 300° C. (total heating time of 24 hours);
32 hour ramp from 25° C. to 300° C., 4 hour hold at 300° C. (total heating time of 36 hours);
44 hour ramp from 25° C. to 300° C., 4 hour hold at 300° C. (total heating time of 48 hours);
68 hour ramp from 25° C. to 300° C., 4 hour hold at 300° C. (total heating time of 72 hours);
24 hour ramp from 25° C. to 300° C., 1 hour hold at 300° C. (total heating time of 25 hours);
20 hour ramp from 25° C. to 400° C., 4 hour hold at 400° C., wherein the total heating time is 24 hours;
32 hour ramp from 25° C. to 400° C., 4 hour hold at 400° C., wherein the total heating time of 36 hours);
44 hour ramp from 25° C. to 400° C., 4 hour hold at 400° C., wherein the total heating time of 48 hours);
68 hour ramp from 25° C. to 400° C., 4 hour hold at 400° C. (total heating time of 72 hours);
24 hour ramp from 25° C. to 400° C., 1 hour hold at 400° C. (total heating time of 25 hours);
20 hour ramp from 25° C. to 500° C., 4 hour hold at 500° C. (total heating time is 24 hours);
32 hour ramp from 25° C. to 500° C., 4 hour hold at 500° C. (total heating time of 36 hours);
44 hour ramp from 25° C. to 500° C., 4 hour hold at 500° C. (total heating time of 48 hours);
68 hour ramp from 25° C. to 500° C., 4 hour hold at 500° C. (total heating time of 72 hours); and
24 hour ramp from 25° C. to 500° C., 1 hour hold at 500° C. (total heating time of 25 hours.

In certain embodiments, the stepwise low temperature heat treatment will include slowly ramping up to various temperatures before reaching a plateau ("a first treatment temperature"), slowly heating again to a higher temperature ("a second treatment temperature") before reaching a plateau and holding at that temperature for a specified period of time, etc. The heating profiles may include, e.g., the following heating profiles:

24 hour ramp from 25° C. to 400° C., 10 hour hold at 400° C., 10 hour ramp from 400° C. to 500° C., 1 hour hold at 500° C. (total heating time of 45 hours);
5 hour ramp from 25° C. to 400° C., 5 hour hold at 400° C., 5 hour ramp from 400° C. to 500° C., 5 hour hold at 500° C. (total heating time of 20 hours);
10 hour ramp from 25° C. to 400° C., 10 hour hold at 400° C., 10 hour ramp from 400° C. to 500° C., 10 hour hold at 500° C. (total heating time of 40 hours);
15 hour ramp from 25° C. to 400° C., 15 hour hold at 400° C., 15 hour ramp from 400° C. to 500° C., 15 hour hold at 500° C. (total heating time of 60 hours);
20 hour ramp from 25° C. to 400° C., 20 hour hold at 400° C., 20 hour ramp from 400° C. to 500° C., 20 hour hold at 500° C. (total heating time of 80 hours);
5 hour ramp from 25° C. to 200° C., 5 hour hold, 5 hour ramp to 300° C., 5 hour hold, 5 hour ramp to 400° C., 5 hour hold;
5 hour ramp from 25° C. to 200° C., 5 hour hold, 5 hour ramp to 300° C., 5 hour hold, 5 hour ramp to 400° C., 5 hour hold, 5 hour ramp to 500° C., 5 hour hold;
10 hour ramp from 25° C. to 200° C., 10 hour hold, 10 hour ramp to 300° C., 10 hour hold, 10 hour ramp to 400° C., 10 hour hold, 10 hour ramp to 500° C., 10 hour hold;
15 hour ramp from 25° C. to 200° C., 15 hour hold, 15 hour ramp to 300° C., 15 hour hold, 15 hour ramp to 400° C., 15 hour hold, 15 hour ramp to 500° C., 15 hour hold;
20 hour ramp from 25° C. to 200° C., 20 hour hold, 20 hour ramp to 300° C., 20 hour hold, 20 hour ramp to 400° C., 20 hour hold, 20 hour ramp to 500° C., 20 hour hold;

In certain further embodiments, the heating profiles may include the following:
rapid heating preferably between 200° C. and <500° C.; most preferable between 300° C. and 400° C.;
stepwise heating from 25° C. to 400° C. with a 4 hour hold at 400° C. with total heating times ≥36 hours; and
10 hour ramp from 25° C. to 200° C., 10 hour hold, 10 hour ramp to 300° C., 10 hour hold, 10 hour ramp to 400° C., 10 hour hold.

In certain further embodiments, alternatively or in addition to the low temperature heat treatments (stepwise heating and or rapid heating), the solgel-derived bioactive glass-ceramic may be treated with an ultraviolet (UV) light. The UV light breaks down the organic residuals and/or impurities in the solgel-derived bioactive glass-ceramic, resulting in carbon dioxide and water, which is then removed by additional heat treatments as described above. The solgel-derived bioactive glass-ceramic may be treated in an UV chamber (e.g., NovaScan UV Chamber) for time periods of about 1, 2, 3, 4, 5, 6, 7, 8, 9, 10, 16, 25, 50, 75, and or 100 hours. It is to be understood that any time period between the time periods listed, as well as longer time periods, are also contemplated.

In certain further embodiments, alternatively or in addition to a low temperature heat treatments (stepwise heating and or rapid heating) and or an UV light treatment, the solgel-derived bioactive glass-ceramic may also be treated with $scCO_2$. Some exemplary treatment conditions are provided in the Examples section below and include, e.g., the following conditions:

(i) 5 hr scCO2+25 mL water misted+16 mL Gent (NovaSterilis) (13.5-18.5% peracetic acid and 4-6% hydrogen peroxide)→Rapid depressurization (less than 45 minutes); and (ii) 5 hr scCO2+25 mL water misted—No peracetic acid→Rapid depressurization (less than 45 minutes).

In certain further embodiments, alternatively or in addition to a low temperature heat treatments (stepwise heating and or rapid heating), the UV light treatment, and or the $scCO_2$ treatment, the solgel-derived bioactive glass-ceramic may also be treated with oxidizers, such as peroxide and or peracetic acid. Other oxidizers are also contemplated. Exemplary treatment conditions are provided in the Examples below.

a. Immersing the solgel-derived bioactive glass-ceramic in 5% hydrogen peroxide for periods 1, 2, 4, 8, 12, 16, 20, 24, 48, 72, or 96 hours
b. Immersing the solgel-derived bioactive glass-ceramic in 10% hydrogen peroxide for periods 1, 2, 4, 8, 12, 16, 20, 24, 48, 72, or 96 hours
c. Immersing the solgel-derived bioactive glass-ceramic in 15% hydrogen peroxide for periods 1, 2, 4, 8, 12, 16, 20, 24, 48, 72, or 96 hours
d. Immersing the solgel-derived bioactive glass-ceramic in 20% hydrogen peroxide for periods 1, 2, 4, 8, 12, 16, 20, 24, 48, 72, or 96 hours
e. Immersing the solgel-derived bioactive glass-ceramic in 25% hydrogen peroxide for periods 1, 2, 4, 8, 12, 16, 20, 24, 48, 72, or 96 hours
f. Immersing the solgel-derived bioactive glass-ceramic in 30% hydrogen peroxide for periods 1, 2, 4, 8, 12, 16, 20, 24, 48, 72, or 96 hours
g. Immersing the solgel-derived bioactive glass-ceramic in 35% hydrogen peroxide for periods 1, 2, 4, 8, 12, 16, 20, 24, 48, 72, or 96 hours In reference to the treatment of the solgels glass-ceramic with oxidizers, longer treatment times than the ones exemplified above are also contemplated.

In certain embodiments, the individual treatments and or a combination of treatments result in an increased surface area of the solgel-derived bioactive glass-ceramic as compared to a melt-derived bioactive glass-ceramic or conventionally treated solgel-derived bioactive glass-ceramic. The terms "increased surface area of the solgel-derived bioactive glass-ceramic" or "increased surface area" in reference to solgel-derived bioactive glass-ceramics refer to solgel glass-ceramics that upon the described treatments possess a surface area greater than about 12 $m^2/g$.

In certain embodiments, the solgel bioactive glass-ceramic processed according to the described treatment methods may be sodium based solgel 45S5 bioactive glass-ceramic and comprise 45% $SiO_2$, 6% $P_2O_5$, 24.5% CaO, and 24.5% $Na_2O$. Other solgel bioactive glass-ceramics may also be processed as described. For example, borate bioactive glass-ceramic (45S5B1), in which the $SiO_2$ of 45S5 bioactive glass-ceramic is replaced by $B_2O_3$ may also be treated by the described extended low temperature heat treatments (rapid and stepwise), ultraviolet (UV) light treatment, a supercritical carbon dioxide ($scCO_2$) treatment, treatment with oxidizers, or a combination of the treatments.

Solgel-derived bioactive glass-ceramic can be prepared by the processes known in the art and briefly described in the background. For example, U.S. Pat. No. 5,074,916, the subject matter of which is incorporated herein by reference, discloses solgel processing techniques used to produce alkali-free bioactive glass-ceramic compositions based on $SiO_2$, $CaO_2$ and $P_2O_5$. U.S. Methods of manufacturing near equilibrium dried solgel bioactive glass-ceramics are described in U.S. Pat. No. 6,171,986, which is herein incorporated by reference in its entirety.

Alternative methods of making sodium solgel-derived bioactive glass-ceramics were previously described in U.S. Pub. Nos. 2014-0271912A1 and 2014-0302165A1, both to Pomrink et al., which are incorporated herein in their entirety. Methods of preparing borate solgel-derived bioactive glass-ceramics were previously described in U.S. Pub. No. 2014-0271913 A1 to Pomrink et al., which also incorporated herein in its entirety.

Specifically, in certain embodiments, the solgel-derived bioactive glass-ceramic can be prepared by mixing a solgel bioactive glass-ceramic precursor including a source of Si, Ca, P, and Na. Borate solgel-derived bioactive glass-ceramics can also be prepared by mixing a solgel bioactive glass-ceramic precursor including a source of borate, instead of sodium.

Many organosodium or inorganic sodium salts may be used as a precursor including but not limited to sodium chloride, sodium ethoxide or sodium silicate. Other precursors of sodium include other sodium organometallics (e.g., sodium methoxide, and sodium tert-butoxide), sodium salts (e.g., sodium hydroxide, and sodium oxalate), sodium nitrates (e.g., sodium nitrate), sodium sulfates (e.g., sodium sulfate, sodium thiosulfate, and sodium dodecyl sulfate), sodium carbonates (e.g., sodium bicarbonate, soda ash, and baking soda) and others, such as sodium silicates and sodium acetate. Such precursors may be used in an amount sufficient to yield 0-40%, 1-55%, 5-15%, 25-30%, or about 25% by weight $Na_2O$ in the bioactive sol gel glass-ceramic.

Exemplary source of silicate (Si) include, but is not limited to, tetraethoxysilane, tetraethylorthosilicate (TEOS), tetramethylorthosilicate (TMOS), fumed silica, colloidal silica, silica gel, sodium silicate, and silicon tetrachloride.

Calcium precursors include but are not limited to organocalcium compounds or inorganic salts of calcium such as calcium nitrate ($Ca(NO_3)_2$), calcium nitrate tetrahydrate ($CaNo_3.4H_2O$), calcium sulphate ($CaSO_4$), calcium silicates or a source of calcium oxide (Lime). Other precursors of calcium include calcium organometallics (e.g., calcium methoxide), calcium salts (e.g., calcium chloride dihydrate, calcium hydroxide, calcium oxolate hydrate, and calcium citrate tetrahydrate), calcium nitrates (e.g., calcium nitrate tetrahydrate), calcium sulfates (e.g., calcium sulfate dehydrate), calcium carbonates (e.g., calcium carbonate) and other precursors, such as calcium acetate hydrate. A source of calcium oxide includes any compound that decomposes to form calcium oxide. Release of $Ca^{2+}$ ions from the surface of the bioactive glass-ceramic aids the formation of the calcium phosphate-rich layer on the surface of the glass-ceramic. The provision of calcium ions by the bioactive glass-ceramic can increase the rate of formation of the calcium phosphate-rich layer. However it should be appreciated that the calcium phosphate-rich layer can form without the provision of calcium ions by the bioactive glass-ceramic, as body fluid itself contains calcium ions. Thus, for the purposes of this invention, bioactive glass-ceramics containing no calcium can be used. The calcium precursor may be present in the precursor in an amount sufficient to yield at least 5%, 0-40%, 10-20%, 20-30% or about 25% CaO in the resultant sol-gel glass-ceramic.

Phosphate precursors include many organophosphates and inorganic phosphate salts including but not limited to triethylphosphate and/or polyphosphates, such as, e.g. sodium hexametaphosphate. Release of phosphate ions from the surface of the bioactive glass-ceramic aids in the formation of hydroxycarbonated apatite. While hydroxycarbonated apatite can form without the provision of phosphate ions by the bioactive glass-ceramic, as body fluid itself contains phosphate ions, the provision of phosphate ions by the bioactive glass-ceramic increases the rate of formation of hydroxycarbonated apatite. The phosphate precursor may be present in an amount sufficient to yield at 0-80%, 0-50%, 20-70%, 20-30%, 25-30%, or about 25% $P_2O_5$ in the resultant glass-ceramic.

The solgel bioactive glass-ceramic may include boron. The boron precursors include but are not limited to organoborate compounds, inorganic borate salts, boric acid, and trimethyl borate. A sufficient amount of boron precursor may be used sufficient to provide $B_2O_3$ in amounts of at least 25%, 30% to 50%, 35-45%, or up to 80% by weight in the glass-ceramic.

The solgel-derived bioactive glass-ceramics may also include one or more of K, Mg, B, F, Ag, Au, Ce, Ba, Ti, Cu, Fe, Mn, Mo, Sr, Zr and Zn. When present, such sources include organometallic and inorganic salts thereof. Each may be present to provide in 0.01 to 20% or more by weight of the respective oxide in the glass-ceramic.

The solgel bioactive glass-ceramic may also include zinc. Zinc precursors include but are not limited to organozinc compounds or inorganic salts containing zinc such as zinc nitrate ($Zn(NO_3)_2$), zinc sulphate ($ZnSO_4$), and zinc silicates and any such compounds that decompose to form zinc oxide. When present, the zinc precursor should be present in amounts sufficient to yield 0.01-5% ZnO in the glass-ceramic.

The bioactive glass-ceramic may include magnesium. Magnesium precursors include but are not limited to organomagnesium compounds or inorganic magnesium salts such as magnesium nitrate ($Mg(NO_3)_2$), magnesium sulphate ($MgSO_4$), magnesium silicates and any such compounds that decompose to form magnesium oxide. When included the magnesium source should be present in an amount sufficient to yield 0.01 to 5% MgO in the bioactive glass-ceramic.

The solgel bioactive glass-ceramic may include boron. The boron precursors include but are not limited to organoborate compounds, inorganic borate salts, boric acid, and trimethyl borate. A sufficient amount of boron precursor may be used sufficient to provide $B_2O_3$ in amounts of at least 25%, 30% to 50%, 35-45%, or up to 80% by weight in the glass-ceramic.

The bioactive glass-ceramic of the present invention may comprise fluorine. Fluorine precursors include but are not limited to organofluorine compounds or inorganic fluorine salts such as calcium fluoride ($CaF_2$), strontium fluoride ($SrF_2$), magnesium fluoride ($MgF_2$), Sodium fluoride (NaF) or potassium fluoride (KF). Fluoride stimulates osteoblasts, and increases the rate of hydroxycarbonated apatite deposition. When present, an amount of fluorine precursor is used to provide 0-35% or 0.01-5% calcium fluoride.

The following bioactive glass-ceramic composition, having a weight % of each element in oxide form in the range indicated, will provide one of several bioactive glass-ceramic compositions that may be used to form the solgel bioactive glass-ceramic used in the described methods of extended low temperature heat treatment:
$SiO_2$ 0-86
CaO 4-35
$Na_2O$ 0-35
$P_2O$, 2-15
$CaF_2$ 0-25
$B_2O_3$ 0-75
$K_2O$ 0-8
MgO 0-5
CaF 0-35

Furthermore, in certain embodiments, metallic materials, such as gold, silver, platinum, copper, palladium, iridium, strontium, cerium, or isotopes, or alloys, or salts thereof, may be incorporated (e.g., either by coating the surface of the bone grafting composition or by including or integrating the metallic materials in the structure of the bone grafting composition) into the solgel-derived bioactive glass-ceramics. These materials are able to conduct an electrical current and prevent or reduce body's inflammatory response at or near the injury site upon the delivery of the solgel-derived bioactive glass-ceramic comprising a metallic material, enhancing the activity of, e.g., the calcium salt and the bone healing process. When bone is injured, it generates an electrical field. This low-level electrical field is part of the body's natural process that stimulates bone healing. When this healing process fails to occur naturally, a conductive implant material can facilitate regeneration of the bone. Conductive implants provide a safe, treatment that helps promote healing in fractured bones and spinal fusions which may have not healed or have difficulty healing. The devices stimulate the bone's natural healing process by sending low-level pulses of electromagnetic energy to the injury or fusion site. Importantly, electrical conductance and reduction of inflammation at the site of a wound may increase the rate at which the wound heals. Metallic materials may also promote wound healing by initiating or promoting angiogenesis. Increased blood flow may increase the rate of wound healing. Other benefits of gold may also be present. The term "metallic material" refers to pure metals, such as gold, silver, platinum, copper, palladium, iridium, strontium, cerium or isotopes (including radioisotopes), or alloys, or salts (the ionic chemical compounds of metals) thereof or other metallic materials having an atomic mass greater than about 45 and less than about 205. The term "atomic mass" is the mass of an atomic particle, sub-atomic particle, or molecule. It is commonly expressed in unified atomic mass units (u) where by international agreement, 1 unified atomic mass unit is defined as 1/12 of the mass of a single carbon-12 atom (at rest). The metallic material may be present in approximate amounts of 0.001-20 wt. % ratio with reference to the total weight of the composition. Alternatively, the metallic material may be present in approximate amounts of 0.001-10 wt. % ratio with reference to the total weight of the composition. The metallic material may also be present in a weight ratio of less than 10 wt. %; less than about 5 wt. %; less than about 2.5 wt. %; less than about 1 wt. %; or less than about 0.5 wt. %. In some embodiments, the weight ratio may be about 0.1%, about 0.2%, about 0.3%, about 0.4%, about 0.5%, about 0.6%, about 0.7%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.5%, about 4%, about 4.5%, or about 5%.

The bioactive solgels processed through the described treatment methods may be further combined (before, during or after the treatments) with a bioactive agent. The bioactive agent comprises one of antibodies, antigens, antibiotics, wound sterilization substances, thrombin, blood clotting factors, conventional chemo- and radiation therapeutic drugs, VEGF, antitumor agents such as angiostatin, endostatin, biological response modifiers, and various combinations thereof.

In certain embodiments, the bioactive solgels processed through the described treatment methods may be further combined (before, during or after the treatments) with polymers to provide further structural support. For example, porous bioactive glass-ceramic hemostatic agents may be prepared by a solgel process described herein that further uses a block copolymer of ethyleneoxide and propyleneoxide.

In certain further embodiments, the bioactive solgels processed through the described treatment methods may be further combined (before, during or after the treatments) with glycosaminoglycans. U.S. Pub. No. 2014-0079789A1 to Pomrink et al., which is incorporated herein in its entirety, provides examples of bioactive glass-ceramics with glycosaminoglycans (GAGs). GAGs are polysaccharides that are present in various cells. There are many different types of GAGs have been found in tissues and fluids of humans, animals, and other vertebrates. GAGs are typically linear molecules with greatly varying chain lengths composed of heterogeneous polysaccharides and are formed by long disaccharide units with varying degrees of linkage, acetylation, and sulfation. The disaccharide units include galactose, N-acetylglucosamine, N-acetylgalactosamine, and glucuronic add. GAGs are often classified as being sulfated or non-sulfated. Known GAGs have been classified as being one of chondroitin sulfate, keratan sulfate, dermatan sulfate, hyaluronic acid, heparin, and heparan sulfate. Along with collagen, GAGs provide significant structural support to animal tissue. Without GAGs, tissues would not undergo proper repair. Further, the protection and maintenance of all tissues depends upon GAGs. Thus. GAGs can serve to provide further support to wounded tissue, particularly in the context of wounded tissue at or near the site of a bone injury.

The solgel-derived bioactive glass-ceramic processed through the described treatment methods may be in a form of particles, spheres, fibers, mesh, sheets or a combination of these forms i.e. fibers within a sphere. The composition, porosity and particle sizes of the bioactive glass-ceramic may vary.

The solgel bioactive glass-ceramic processed through the described treatment methods may vary in size. For example, the particles of the bioactive glass-ceramic may range in size from 0.01 µm to 5 mm. Other ranges include about 1-5 micrometers, about 5-15 micrometers, about 15-50 micrometers, about 50-200 micrometers, about 200-1,000 micrometers, about 1-2 millimeters, about 2-3 millimeters, about 3-4 millimeters, or about 4-5 millimeters. In some embodiments, the bioactive glass-ceramic particle has a diameter of between about 0.01 micrometer and about 5,000 micrometers.

In certain embodiments, the bioactive glass-ceramic may include 0-80%<100 µm, 0-80%<500 µm, 0-80% 500-1000 µm, 0-80% 1000-2000 µm, 0-80% 2000-5000 µm, 0-90% 90-710 µm, and 0-90% 32-125 µm bioactive glass-ceramic.

In certain embodiments, the bioactive solgels processed using the described treatment methods are hemostatic materials that are bioabsorbable, that provide for superior hemostasis, and may be fabricated into a variety of forms suitable for use in controlling bleeding from a variety of wounds, both internal and external. For example, in vascular surgery, bleeding is particularly problematic. In cardiac surgery, the multiple vascular anastomoses and cannulation sites, complicated by coagulopathy induced by extracorporeal bypass, can result in bleeding that can only be controlled by topical hemostats. Rapid and effective hemostasis during spinal surgery, where control of osseous, epidural, and/or subdural bleeding or bleeding from the spinal cord is not amenable to sutures or cautery, can minimize the potential for injury to nerve roots and reduce the procedure time. In liver surgery, for example, live donor liver transplant procedures or removal of cancerous tumors, there is a substantial risk of massive bleeding. An effective hemostatic material can significantly enhance patient outcome in such procedures. Even in those situations where bleeding is not massive, an effective hemostatic material can be desirable, for example, in dental procedures such as tooth extractions, as well as the treatment of abrasions, burns, and the like. In neurosurgery, oozing wounds are common and are difficult to treat.

As such, certain embodiments relate to a method of improving or enhancing hemostasis in a patient (e.g., undergoing a surgery) by using the solgel-derived bioactive glass-ceramic processed using the treatment methods, the solgel-derived bioactive glass-ceramic having at least 0.1% and up to 100% of organic residuals and or impurities have been removed from the bioactive glass-ceramic; in certain embodiments being substantially free of any organic residuals and or impurities (i.e., at least 90% of organic residuals and or impurities have been removed from the bioactive glass-ceramic).

Bioactive solgel glass-ceramics may be in granular or particulate form, matt or fiber form, a hemostatic sponge, incorporated into a foam, or in the form of a paste or putty. The solgel glass-ceramics may also be in a form of a sphere or a bead. They may also be formulated into settable and non-settable carriers.

In certain alternative embodiments, the solgel-derived bioactive glass-ceramic prepared using the described treatment methods may be suitable for use in soft tissue repair. As such, certain embodiments relate to a method of treating a soft tissue injury in a patient using the solgel-derived bioactive glass-ceramic prepared using the treatment methods, the solgel-derived bioactive glass-ceramic having at least 0.1% and up to 100% of organic residuals and or impurities have been removed from the bioactive glass-ceramic; in certain embodiments being substantially free of any organic residuals and or impurities (i.e., at least 90% of organic residuals and or impurities have been removed from the bioactive glass-ceramic).

Other uses for the solgel compositions of the present invention include filling bone defects, bone repair/regeneration, limb salvage, drug delivery, repair of osteochondral defects, repairing osseous defects, dental hypersensitivity, tooth whitening, and guided tissue regeneration.

EXAMPLES

Definitions

45S5 Glass-ceramic: 45% $SiO_2$, 6% $P_2O_5$, 24.5% CaO, 24.5% $Na_2O$
DHT: Dehydrothermal treatment
BET: Brunauer-Emmett-Teller gas absorption theory
LOD: Loss on Drying
LOI: Loss on Ignition
$scCO_2$: Supercritical carbon dioxide
UV: Ultraviolet Example 1

This was a screening study for the effects of extended, low temperature heating on the surface area and material removal for solgel-derived 45S5 bioactive glass-ceramics. One or two samples were typically tested for each condition.

Overview

A variety of new solgel-derived 45S5 solutions were prepared at Particle Solutions and subjected to low temperature heat treatments (<600° C.) for extended periods of time to assess the removal of organic residuals and specific surface areas.

All solgel samples consisted of sodium silicate and calcium lactate in addition to being gelled with lactic acid while drying process conditions varied: 150420-01 was air dried in ambient conditions, 150725-01 was a scale-up of 150420-01 delivered as a wet gel, 150604-01 was steam back pressure dried (150° C.), and 150601-01 was delivered as a wet gel and subjected to dehydrothermal treatment (105° C. and 150 mTorr) and lyophilization processes prior to heat treatment.

The solgel glass-ceramics were heated at temperatures of 200° C., 300° C., 400° C., and 500° C. for periods of five and seven days; additional time points were recorded for several samples. Following heat treatment, final weights were recorded and the extent of removal of the organic components was determined along with the specific surface areas. Surface area was measured using a Quantachrome NOVA 2000 by BET analysis to determine changes in pore structure.

Materials:
Solgel-derived 45S5 samples
Lyophilizer
Lindberg Blue M Box Furnace
Crucibles
Analytical balance
Quantachrome NOVA 2000 Gas Sorption Analyzer The solgel solutions were prepared by Particle Solutions for testing at a laboratory.

Test and Control Samples

Control and test sample selection criteria were as follows:

Control samples consisted of 45S5 glass-ceramic powders that had not yet been subjected to extended heat treatments. All samples contained sodium silicate and calcium lactate in addition to being gelled with lactic acid.

Sample A (150420-01) was air dried in ambient conditions

Sample B (150725-01) was a scale-up of sample A delivered as a wet gel

Sample C (150604-01) was steam back pressure dried at 150° C.

Sample D (CG-02-33-DHT) was 150604-01 subjected to dehydrothermal treatment

Sample E (CG-02-35-LYO) was 150604-01 subjected to a lyophilization process

Test samples consisted of control samples heated to various temperatures for extended periods of time.

Note that not all samples were tested at all temperatures and times and specific surface area measurements were not taken for all samples due to time constraints.

1. 200° C. for 4 hours, 1 day, 2 days, 5 days, and 7 days
2. 300° C. for 3 days, 5 days, and 7 days
3. 400° C. for 5 days and 7 days
4. 500° C. for 5 days and 7 days Samples D and E were subjected to DHT and lyophilization, respectively, using the MillRock RD85 Lyophilizer.

1. DHT was performed at 150° C. for 24 hours.
2. Lyophilization was performed at −35° C. followed by a drying cycle at 25° C.

Samples were heat treated using the Lindberg Blue M Box furnace using programmable stepwise heating profiles.

The samples were processed and percent material removed was analyzed for the heat treatments by recording sample weights before and after the heat treatments.

Specific surface areas were measured using the Quantachrome Nova 2200e Gas Adsorption Surface Area Analyzer; NovaWin software implemented BET calculations to determine specific surface areas.

Conditions

Samples were heat to various temperatures for extended periods of time (200 to 500° C. for time periods from 4 hours to 7 days).

Samples were evaluated in the NovaBone Research and Development laboratory in Alachua, Fla. under ambient conditions (20±5° C. with 30-80% RH).

Parameter Selection i. Samples were heated at various temperatures between 200 and 500° C. for time periods from 4 hours to 7 days.

ii. Surface area analysis was performed using the Quantachrome Nova 2200e; samples were subjected to degassing at 120° C. for at least 2 hours prior to analysis.

Test procedures (chronological description when two or more procedures involved).

i. Solgel samples were received from Particle Solutions.
ii. Heat treatments:
1) Crucible weights were recorded.
2) Samples were placed in crucibles and weights were recorded.
3) Samples were individually subjected to the various heating profiles previously outlined.
4) Post heat treatment, the samples were placed in a desiccator to allow the samples to cool under dry ambient conditions.

Final sample weights were recorded and the percentage of material removed was determined based on the weight difference compared to the initial weights.

Specific Surface Area Measurements:

Samples were placed in test cells and placed in the heating pouch on the Quantachrome NOVA 2200e at 120° C. to properly dry the samples prior to surface area analysis.

After drying, sample weights were collected and sample cells were inserted into the testing ports on the Quantachrome NOVA 2200e to collect surface area data.

Specific surface area values were assessed using NovaWin software.

Specific surface area testing was first performed for the control samples (samples not subjected to any heat treatment profiles) to establish baseline surface areas.

Evaluation

Material removal: The samples were removed from the furnace after the appropriate heating time at the desired temperature had been reached. The percentage of material removed was calculated based on remaining sample weight after the sample had cooled to ambient temperature in a desiccator.

Specific surface area: The Quantachrome NOVA 2200e and NovaWin software display surface area data once testing has been completed.

Maximization of specific surface area is desired although a formal acceptance criteria was not established for the percentage of material removed or specific surface area.

Results

Table 1 below contains the surface area data of the solgel samples prior to heat treatment (control samples); 150725-01 was not assessed here since this sample was a scale-up of 150420-01.

TABLE 1

Control Sample Surface Areas

| Sample | Surface Area (m²/g) - Station A | Correlation ($R^2$) - Station A | Surface Area (m²/g) - Station B | Correlation ($R^2$) - Station B |
|---|---|---|---|---|
| 150420-01 | 1.2170 | 0.994200 | 0.9010 | 0.997333 |
| 150604-01 | 3.5630 | 0.999422 | 4.0608 | 0.998210 |
| CG-02-33-DHT | 0.1424 | 0.277000 | 0.3707 | 0.700600 |
| CG-02-35-LYO | <0.001 | Inconclusive | <0.001 | Inconclusive |

Table 2 below contains percent material removed and averaged specific surface areas for the samples tested for 5 day and 7 day periods. These two time points were selected because a majority of the samples were tested at these time points for all temperatures investigated. Note that not at samples were tested at every temperature and heating duration; these samples were not dried at 105° C. prior to heat treating.

TABLE 2

Temperature and Heating Duration Comparison - Material Removed and Specific Surface Area

| Sample | Duration | Total Material Removed (200° C.) | Average Specific Surface Area −200° C. (m2/g) | Total Material Removed (300° C.) | Average Specific Surface Area −300° C. (m2/g) | Total Material Removed (400° C.) | Average Specific Surface Area −400° C. (m2/g) | Total Material Removed (500° C.) | Average Specific Surface Area −500° C. (m2/g) |
|---|---|---|---|---|---|---|---|---|---|
| 150420-01 | 5 days | — | — | 56.64% | 76.895 | 65.46% | 86.757 | 66.16% | 4.970 |
| 150604-01 | 5 days | 24.09% | — | 47.55% | — | 54.51% | 96.752 | 54.33% | 16.863 |
| 150725-01 | 5 days | — | — | — | — | 84.09% | 83.712 | — | — |
| CG-02-33-DHT | 5 days | 36.21% | — | 51.02% | — | — | — | 61.35% | <0.001 |
| CG-02-35-LYO | 5 days | — | — | 54.38% | — | — | — | 60.53% | 0.3244 |
| 150420-01 | 7 days | 46.16% | 100.0183 | 59.02% | 128.063 | 65.61% | 81.498 | 65.56% | 2.884 |
| 150604-01 | 7 days | 29.65% | 61.0463 | 51.48% | 94.648 | 54.99% | 84.696 | 52.41% | 7.559 |
| 150725-01 | 7 days | — | — | — | — | 84.35% | 87.912 | — | — |
| CG-02-33-DHT | 7 days | 38.11% | — | 59.26% | — | — | — | 58.84% | <0.001 |
| CG-02-35-LYO | 7 days | 41.85% | — | 57.71% | — | — | — | 59.89% | 0.2775 |

FIG. 1 displays a bar chart comparison of the percentage of material removed from each sample based upon temperatures and heating times. Note that 20° C. refers to samples that remained at ambient temperature and we not subjected to heat treatment.

Figure 2:
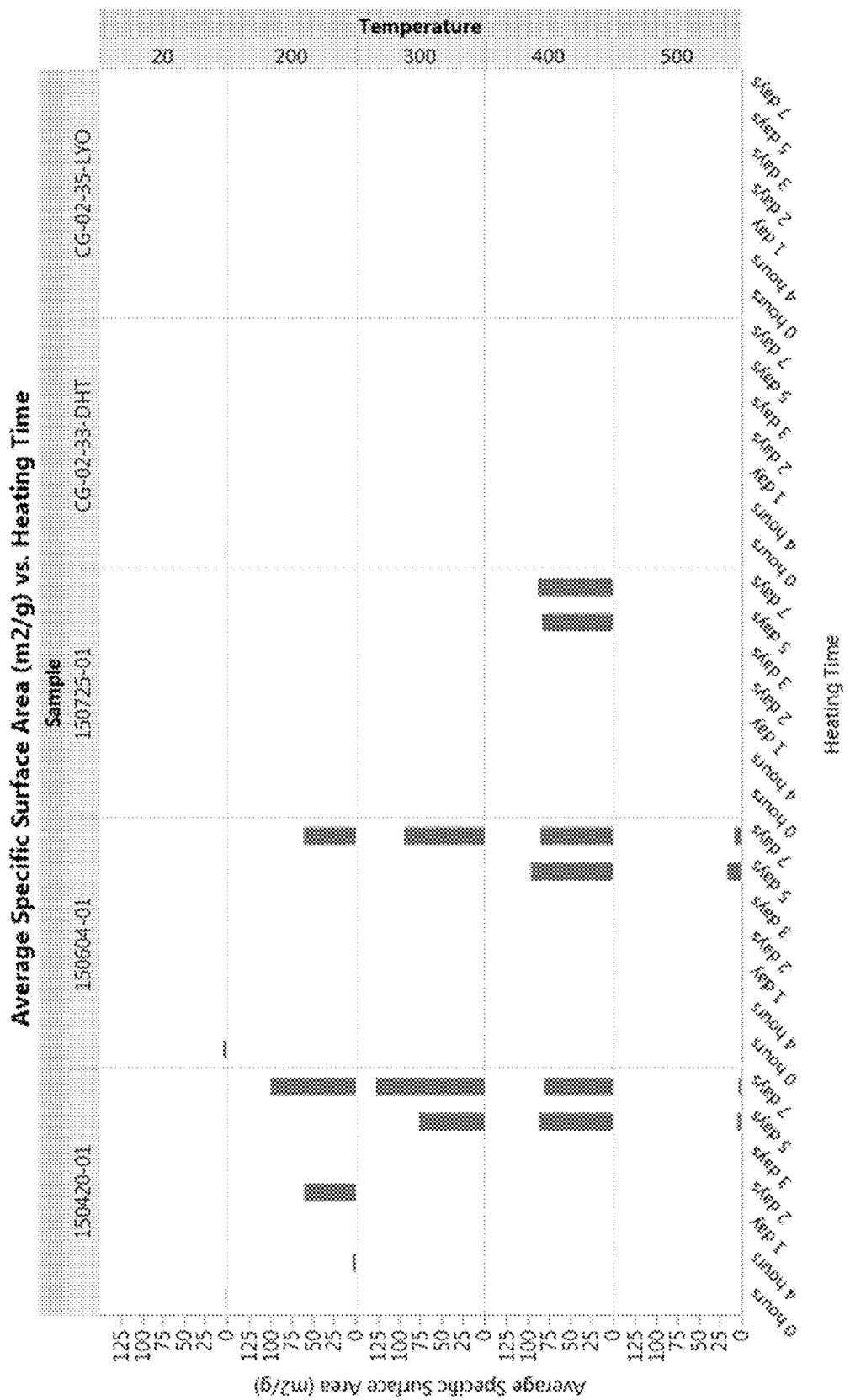
FIG. 2 displays a bar chart comparison of the average specific surface area of each tested solgel-derived bioactive glass-ceramic sample based upon temperatures and heating times. Note that 20° C. refers to samples that remained at ambient temperature and we not subjected to heat treatment.
Figure 3:
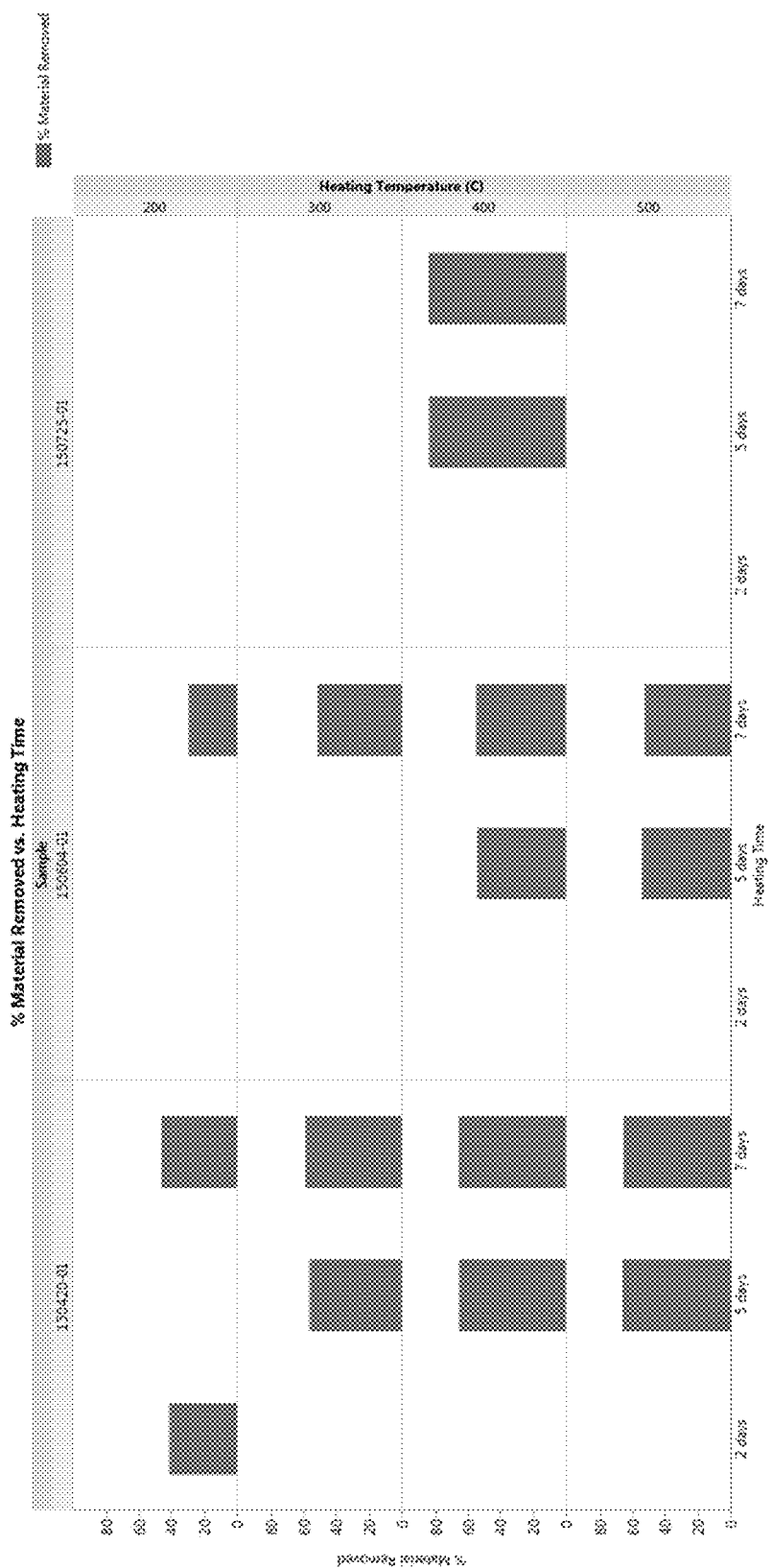
FIG. 3 displays a bar chart comparison of the percentage of material removed from each sample based upon temperatures and heating times.
Figure 4:
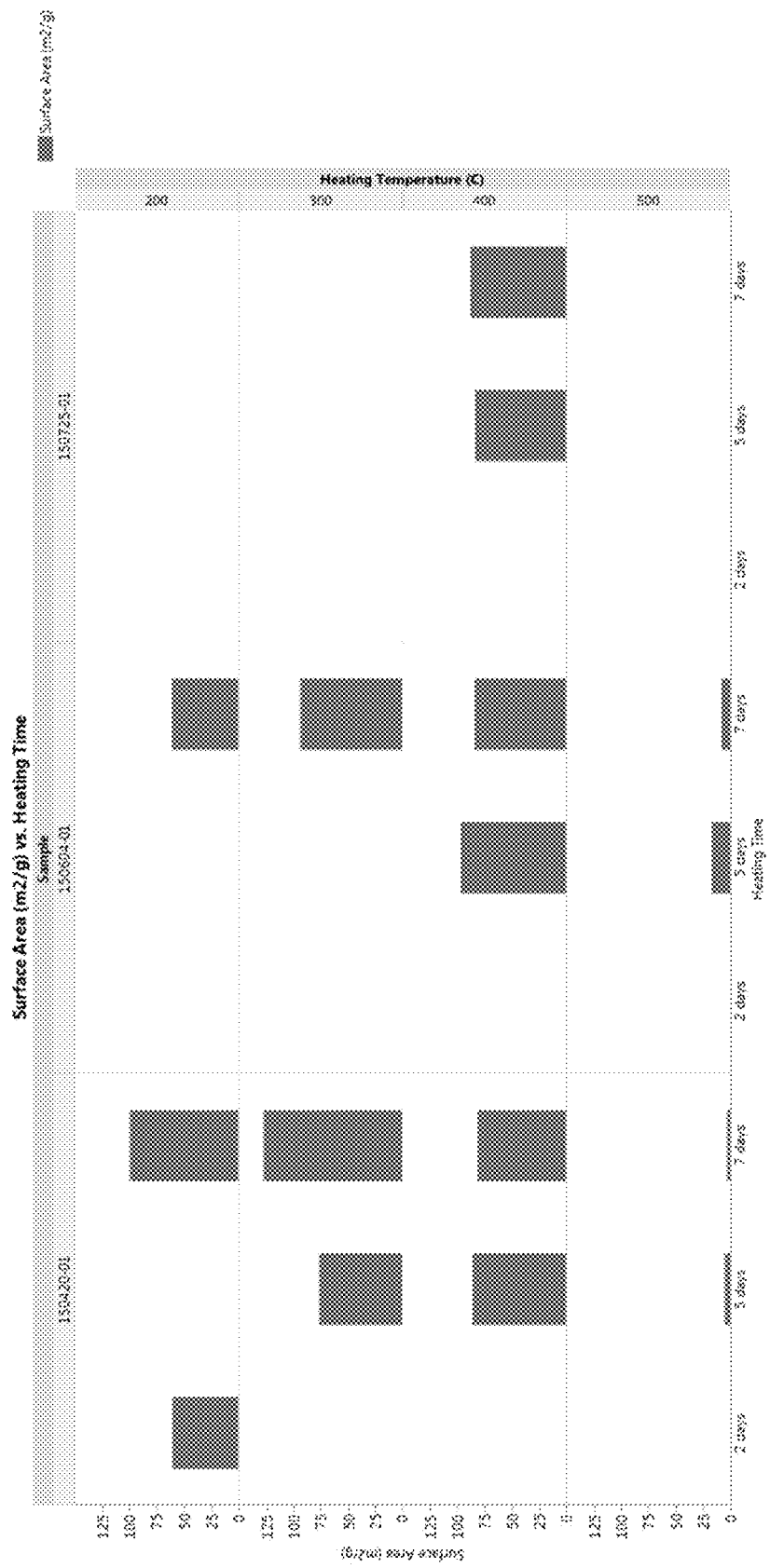
FIG. 4 displays a bar chart comparison of the surface areas of each sample based upon temperatures and heating times.
Figure 5:
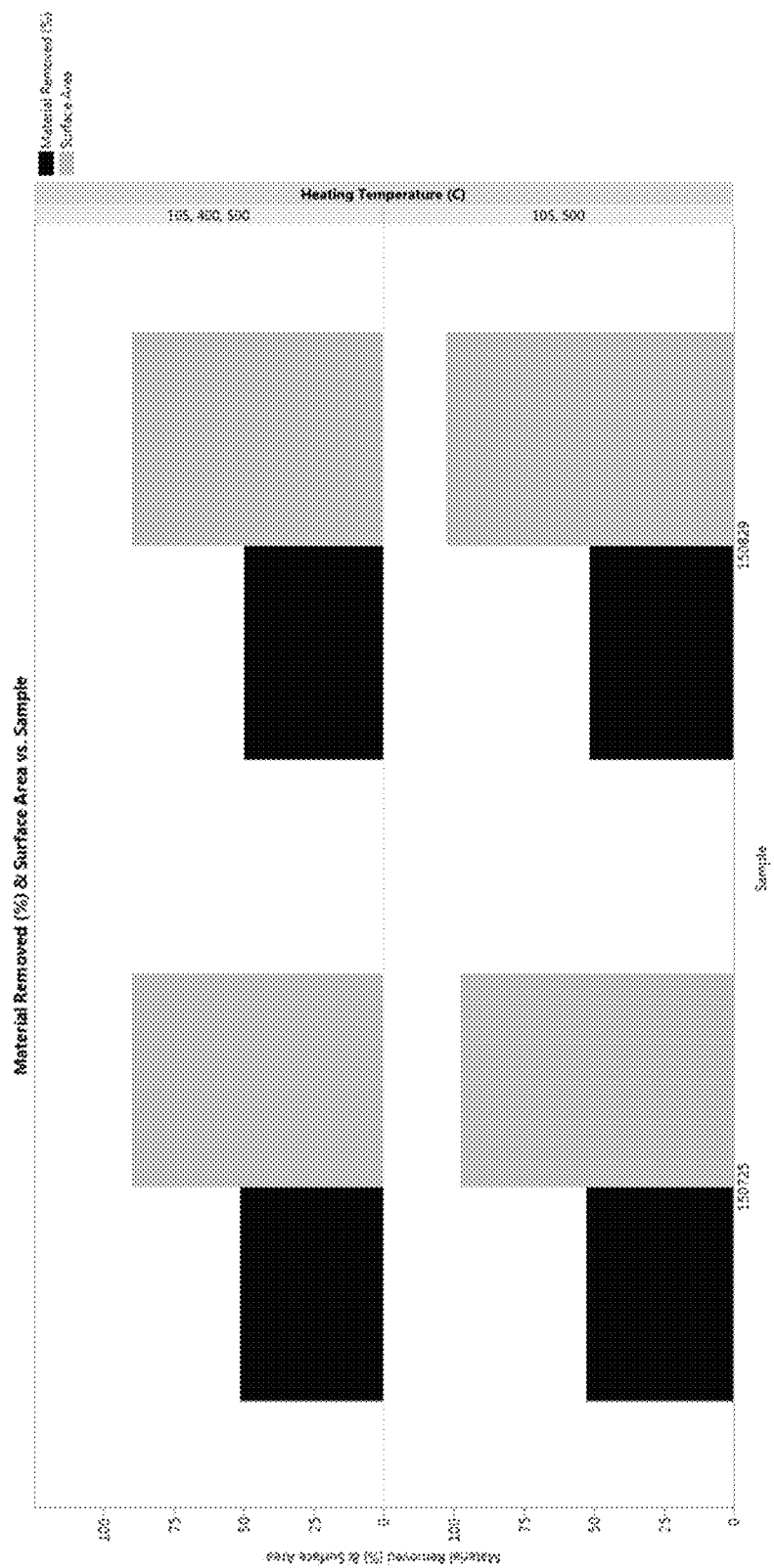
FIG. 5 displays a bar chart comparison of the percentage of material removed and surface areas for each sample subjected to a heat ramp profile.
Figure 6:
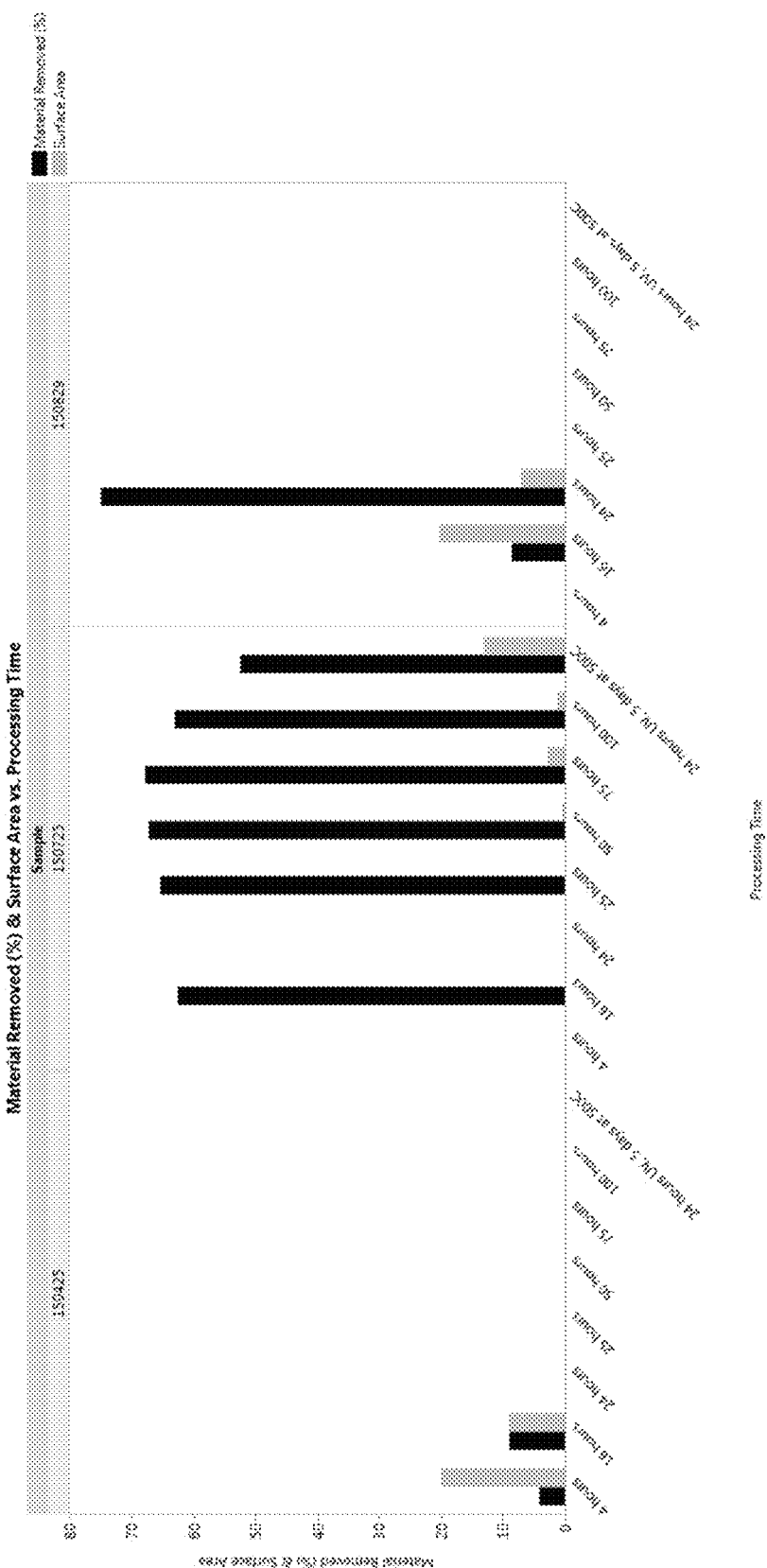
FIG. 6 displays a bar chart comparison of the percentage of material removed and surface areas for each sample subjected to UV treatment.
Figure 7:
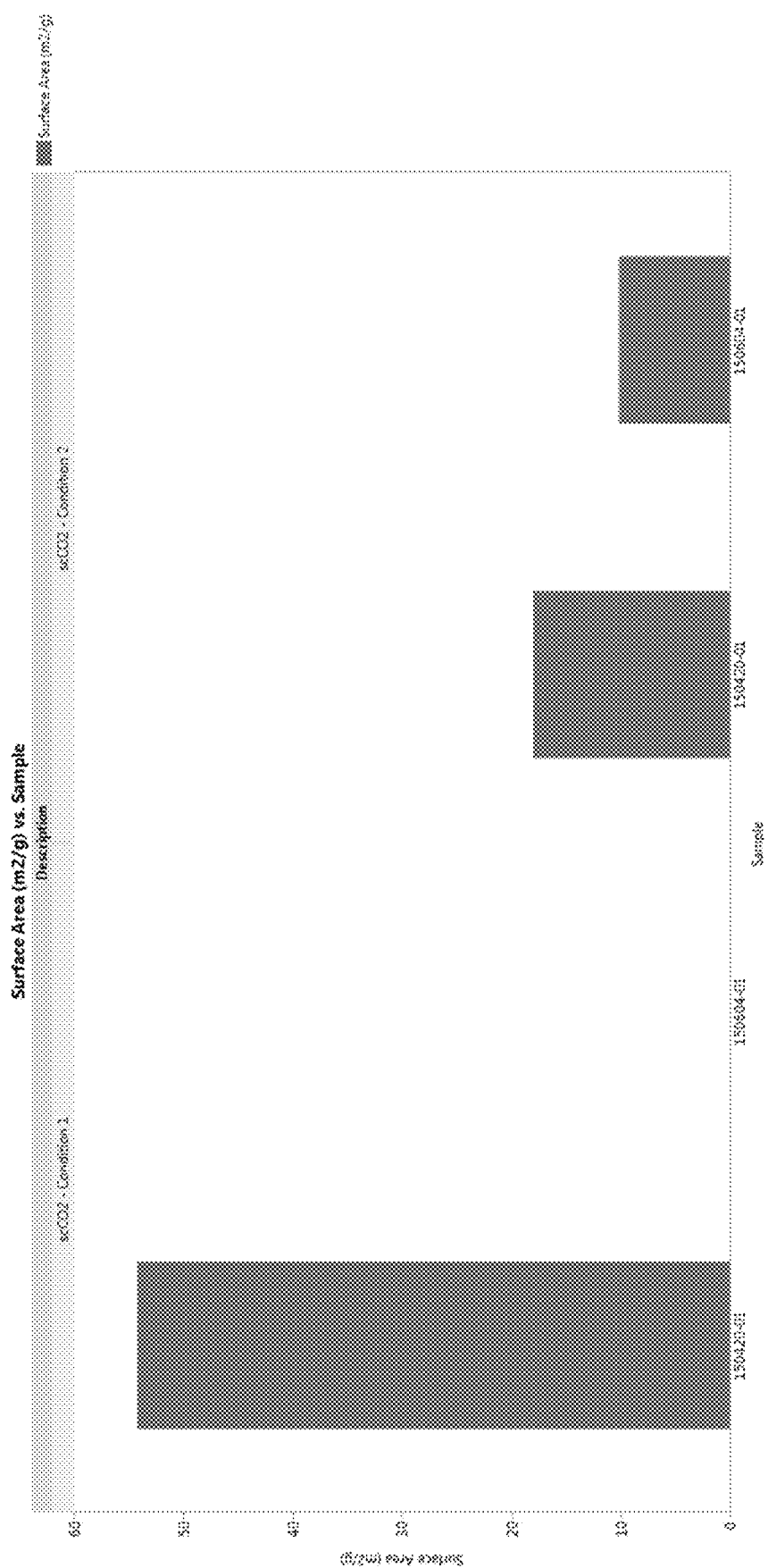
FIG. 7 displays a bar chart comparison of the surface areas for each sample subjected to a $scCO_2$ treatment; percentage of material removed was not displayed as these values were negligible for all samples treated with $scCO_2$.

FIG. 2 displays a bar chart comparison of the average specific surface area of each sample based upon temperatures and heating times. Note that 20° C. refers to samples that remained at ambient temperature and we not subjected to heat treatment.

The percentage of material removed increased with increasing temperature and treatment time with the largest change demonstrated when increasing the temperature from 200° C. to 300° C.; small increases were observed when heating from 300° C. to 400° C. and very little change occurred when heating to 500° C.

In general, the specific surface areas increased when heating to 200° C. and then increased further when heating to 300° C.; heating to 400° C. resulted in marginal increases or decreases in specific surface area compared to 300° C. and a large decrease occurred in specific surface areas values when samples were heated to 500° C.

The results indicate that heating to 400° C. will result in the highest percentage of material removal without significantly compromising the pore structure of the glass-ceramics; heating to 300° C. for 7 days resulted in the maximum surface area for 150420-01, heating to 400° C. for 5 days resulted in the maximum surface area for 150604-01, and the lyophilized and dehydrothermally treated samples exhibited low surface areas (<1.00 m²/g) for all treatment temperatures indicating a collapse of the pore structure of the solgel glass-ceramic.

Example 2

This study was conducted to determine the effects of low temperature, UV and scCO$_2$ treatments on the resulting specific surface areas and removal of organic residuals from solgel-derived 45S and 45S5 glass-ceramics.

All solgel samples consisted of sodium silicate and calcium lactate in addition to being gelled with lactic acid.

Control samples consisted of 45S5 glass-ceramic powders that had not yet been subjected to extended heat treatments. All samples contained sodium silicate and calcium lactate in addition to being gelled with lactic acid:

150420-01 was a 45S sample air dried in ambient conditions, 150725-01 was a scale-up of 150420-01 delivered as a wet gel, 150604-01 was 150420-01 steam back pressure dried (150° C.), 150425-01 was a 45S5 sample air dried in ambient conditions, and 150829-01 was a scale-up of 150425-01 delivered as a wet gel.

Test samples consisted of control samples subjected to various treatments for extended periods of time. Note that not all samples were tested at all temperatures and times and specific surface area measurements were not taken for all samples due to time constraints.

Sample weights were collected before and after treatment to determine the percentage of material removed as a result of the various treatment processes.

Samples were evaluated in a laboratory under ambient conditions (20±5° C. with 30-80% RH).

For the heat treatments, the solgel glass-ceramics were heated at temperatures of 200° C., 300° C., 400° C., and 500° C. for periods of five and seven days; additional time points were recorded for several samples and controlled heat ramping was also explored for several samples:

200° C. for 4 hours, 1 day, 2 days, 5 days, and 7 days;
300° C. for 3 days, 5 days, and 7 days;
400° C. for 5 days and 7 days;
500° C. for 5 days and 7 days;
24 hour dry at 105° C.; 24 hour ramp to 500° C., 1 hour at 500° C.; and
24 hour dry at 105° C.; 24 hour ramp to 400° C., 10 hours at 400° C., 10 hour ramp to 500° C., 1 hour at 500° C.

Crucible weights were recorded.

Samples were placed in crucibles and weights were recorded.

Samples were individually subjected to the various heating profiles outlined above.

Post heat treatment, the samples were placed in a desiccator to allow the samples to cool under dry ambient conditions.

Final sample weights were recorded and the percentage of material removed was determined based on the weight difference compared to the initial weights.

Samples were heat treated using the Lindberg Blue M Box furnace using programmable stepwise heating profiles.

UV samples were subjected to UV light in a NovaScan chamber for time periods of 16, 25, 50, 75, and 100 hours; several samples were also subjected to UV light treatment at Opsytec:

4 and 16 hour treatments at Opsytec; and
16, 25, 50, 75, and 100 hour treatments using NovaScan UV Chamber.

The NovaScan UV chamber was used for internal UV treatments; some samples were also outsourced UV treatments.

UV Treatments (Internal):

Crystallizing dish weights were recorded.

Samples were placed in the crystallizing dishes and weights were recorded.

Samples were individually subjected to the UV treatment profiles outlined above.

Final sample weights were recorded and the percentage of material removed was determined based on the weight difference compared to the initial weights.

UV Treatments (Outsourced):

Samples were shipped to a treatment facility.

Sample weights were recorded prior to UV treatment.

Samples were individually subjected to the UV treatment profiles outlined above.

Final sample weights were recorded and the percentage of material removed was determined based on the weight difference compared to the initial weights.

Supercritical $CO_2$ was Performed on Several Samples:

Condition 1: 5 hr scCO2+25 mL water misted+16 mL Gent (13.5-18.5% peracetic acid and 4-6% hydrogen peroxide)→Rapid depress; and Condition 2: 5 hr scCO2+25 mL water misted–No peracetic acid→Rapid depress.

Sample weights were recorded prior to $scCO_2$ treatment.

Samples were individually subjected to the $scCO_2$ treatment profiles outlined above.

Hydrogen Peroxide was Used to Treat Several Samples:

Samples were subjected to either a 30 or 35% hydrogen soak for at least 24 hours.

Following immersion in hydrogen peroxide, samples were dried for 24 hours at 105° C. to remove the hydrogen peroxide.

Final sample weights were recorded and the percentage of material removed was determined based on the weight difference compared to the initial weights.

Following treatment, final weights were recorded and the extent of removal of the organic components was determined along with the specific surface areas. Surface area was measured by BET analysis using a NOVA 2200e to determine changes in pore structure.

Specific Surface Area Measurements:

Samples were placed in test cells and placed in the heating pouch on the Quantachrome NOVA 2200e at 120° C. to properly dry the samples prior to surface area analysis.

After drying, sample weights were collected and sample cells were inserted into the testing ports on the Quantachrome NOVA 2200e to collect surface area data.

Specific surface area values were assessed using NovaWin software.

Specific surface area testing was first performed for the control samples (samples not subjected to any heat treatment profiles) to establish baseline surface areas.

Evaluation

Table 3 highlights the specific surface area data of the control samples (not subjected to any treatment).

Tables 4, 5, 6, and 7 highlight the percent material removed and specific surface area data for test samples treated with prolonged heating, ramped heating, UV, and $scCO_2$, respectively.

Table 3 contains the surface area data of the solgel samples prior to heat treatment; 150725-01 was not assessed here since this entire batch was utilized for outsourced UV treatment. Table 3 also shows melt-derived 45S5 and solgel 58S results for comparison.

TABLE 3

Control Sample Surface Areas

| Sample | Surface Area ($m^2/g$) | Correlation ($R^2$) |
|---|---|---|
| 150420-01 | 1.0590 | 0.9958 |
| 150604-01 | 3.8119 | 0.9988 |
| 150725-01 | 5.6315 | 0.9983 |
| 150829-01 | 17.029 | 0.9995 |
| 111219-1B - 58S | 166 | >0.99 |
| Melt-derived 45S5 | 2.7 | >0.99 |

Table 4 contains percent material removed and averaged specific surface areas for the samples tested for 5 day and 7 day heat treatment periods. These two time points were selected because a majority of the samples were tested at these time points for all temperatures investigated. Note that not at samples were tested at every temperature and heating duration; these samples were not dried at 105° C. prior to heat treatment.

TABLE 4

Temperature and Heating Duration Comparison - Material Removed and Specific Surface Area

| Sample | Duration | Material Removed (200° C.) | Average Specific Surface Area –200° C. (m2/g) | Material Removed (300° C.) | Average Specific Surface Area –300° C. (m2/g) | Material Removed (400° C.) | Average Specific Surface Area –400° C. (m2/g) | Material Removed (500° C.) | Average Specific Surface Area –500° C. (m2/g) |
|---|---|---|---|---|---|---|---|---|---|
| 150420-01 | 5 days | — | — | 56.64% | 76.895 | 65.46% | 86.757 | 66.16% | 4.970 |
| 150604-01 | 5 days | 24.09% | — | 47.55% | — | 54.51% | 96.752 | 54.33% | 16.863 |
| 150725-01 | 5 days | — | — | — | — | 84.09% | 83.712 | — | — |
| 150420-01 | 7 days | 46.16% | 100.0183 | 59.02% | 128.063 | 65.61% | 81.498 | 65.56% | 2.884 |
| 150604-01 | 7 days | 29.65% | 61.0463 | 51.48% | 94.648 | 54.99% | 84.696 | 52.41% | 7.559 |
| 150725-01 | 7 days | — | — | — | — | 84.35% | 87.912 | — | — |

Table 5 contains the percent material removed and averaged specific surface areas for the samples subjected various heat ramp profiles described above.

TABLE 5

Heat Ramp Profiles - Material Removed and Specific Surface Area

| Test Sample | Temp. (° C.) | Heating Time | % Weight Removed after 105 C. | % Weight Removed after Final Heat Treatment | Total % Weight Removed | Surface Area (m2/g) | Correlation (R2) |
|---|---|---|---|---|---|---|---|
| 150725-01 | 105, 500 | 24 hour dry<br>24 hour ramp to 500 C.<br>1 hour at 500 C. | 66.28% | 52.61% | 84.02% | 97.718 | 0.99994 |
| 150829-01 | 105, 500 | 24 hour dry<br>24 hour ramp to 500 C.<br>1 hour at 500 C. | 79.24% | 51.40% | 89.91% | 102.703 | 0.99992 |
| 150725-01 | 105, 400, 500 | 24 hour dry<br>24 hour ramp to 400 C.<br>10 hour at 400 C.<br>10 hour ramp to 500 C.<br>1 hour at 500 C. | 65.89% | 51.41% | 83.43% | 89.993 | 0.9999 |
| 150829-01 | 105, 400 500 | 24 hour dry<br>24 hour ramp to 400 C.<br>10 hour at 400 C.<br>10 hour ramp to 500 C.<br>1 hour at 500 C. | 79.37% | 49.83% | 89.65% | 90.267 | 0.99986 |
| 150829-01 | 105, 300 | 24 hour dry<br>300 C. for 24 hours (20 hour ramp, 4 hour hold) | 79.24% | 39.26% | 87.39% | 113.894 | 0.99987 |
| 150829-01 | 105, 300 | 24 hour dry<br>300 C. for 48 hours (44 hour ramp, 4 hour hold) | 79.24% | 36.58% | 86.83% | 106.401 | 0.99965 |
| 150829-01 | 105, 300 | 24 hour dry<br>400 C. for 24 hours (20 hour ramp, 4 hour hold) | 79.24% | 49.38% | 89.49% | 73.812 | 0.99977 |
| 150829-01 | 105, 300 | 24 hour dry<br>400 C. for 48 hours (44 hour ramp, 4 hour hold) | 79.24% | 40.57% | 87.66% | 62.655 | 0.99978 |
| 150829-01 | 105, 500 | 24 hour dry<br>500 C. for 24 hours (20 hour ramp, 4 hour hold) | 79.24% | 50.55% | 89.73% | 40.443 | 0.9999 |

TABLE 5-continued

Heat Ramp Profiles - Material Removed and Specific Surface Area

| Test Sample | Temp. (° C.) | Heating Time | % Weight Removed after 105 C. | % Weight Removed after Final Heat Treatment | Total % Weight Removed | Surface Area (m2/g) | Correlation (R2) |
| --- | --- | --- | --- | --- | --- | --- | --- |
| 150829-01 | 105, 500 | 24 hour dry 500 C. for 48 hours (44 hour ramp, 4 hour hold) | 79.24% | 53.60% | 90.37% | 73.24 | 0.99989 |

Table 6 contains the percent material removed and averaged specific surface areas for samples subjected to UV treatment.

TABLE 6

UV Treatments - Material Removed and Specific Surface Area

| Sample | Temp (° C.) | Duration | Material Removed from drying at 105 C. | Material Removed from UV | Material removed from heat | Total Material Removed | Surface Area (m$^2$/g) | Correlation (R$^2$) |
| --- | --- | --- | --- | --- | --- | --- | --- | --- |
| Opsytec Samples | | | | | | | | |
| 150425-01 - 4 hour UV | 50 | 4 hours | 79.24% | 4.05% | N/A | 80.08% | 19.909 | 0.99992 |
| 150425-01 - 16 hour UV | 50 | 16 hours | 79.24% | 8.98% | N/A | 81.10% | 8.980 | 0.99980 |
| Novascan Samples (in-house UV chamber) | | | | | | | | |
| 150725-01 - 16 hour UV | 50 | 16 hours | N/A | 62.54% | N/A | 62.54% | 0.013 | 0.31471 |
| 150725-01 - 25 hour UV | 50 | 25 hours | N/A | 65.42% | N/A | 65.42% | 0.000 | 0.57337 |
| 150725-01 - 50 hour UV | 50 | 50 hours | N/A | 67.23% | N/A | 67.23% | 0.445 | 0.99885 |
| 150725-01 - 75 hour UV | 50 | 75 hours | N/A | 67.85% | N/A | 67.85% | 2.670 | 0.99986 |
| 150725-01 - 100 hour UV | 50 | 100 hours | N/A | 63.07% | N/A | 63.07% | 1.153 | 0.99697 |
| 150829-01 - 24 hour UV | 50 | 24 hours | N/A | 74.91% | N/A | 74.91% | 7.153 | 0.99959 |
| 150829-01 - 16 hour UV after 24 drying at 105 C. | 105 | 16 hours | 79.24% | 8.58% | N/A | 81.02% | 20.194 | 0.99966 |
| 150829-01 - UV 16 hours | 105 (UV) 400 C. (oven) | 16 hours (UV) 400 C. for 36 hours (32 hour ramp, 4 hour hold) | 79.24% | 8.58% | 45.57% | 89.67% | 143.95 | 0.99993 |
| 150829-01 - UV 16 hours | 105 (UV) 300 C. (oven) | UV 16 hours 300 C. for 24 hours (20 hour ramp, 4 hour hold) | 79.24% | 8.58% | 36.83% | 88.01% | 72.07 | 0.99992 |
| 150829-01 - UV 16 hours | 105 (UV) 300 C. (oven) | UV 16 hours 300 C. for 48 hours (44 hour ramp, 4 hour hold) | 79.24% | 8.58% | 26.30% | 86.01% | 57.628 | 0.99992 |

TABLE 6-continued

UV Treatments - Material Removed and Specific Surface Area

| Sample | Temp (° C.) | Duration | Material Removed from drying at 105 C. | Material Removed from UV | Material removed from heat | Total Material Removed | Surface Area ($m^2/g$) | Correlation ($R^2$) |
|---|---|---|---|---|---|---|---|---|
| 150829-01 - UV 16 hours | 105 (UV) 400 C. (oven) | UV 16 hours 400 C. for 24 hours (20 hour ramp, 4 hour hold) | 79.24% | 8.58% | 47.82% | 90.10% | 84.954 | 0.99993 |
| 150829-01 - UV 16 hours | 105 (UV) 400 C. (oven) | UV 16 hours 400 C. for 48 hours (44 hour ramp, 4 hour hold) | 79.24% | 8.58% | 40.03% | 88.62% | 64.708 | 0.99985 |

Table 7 contains the percent material removed and averaged specific surface areas for the samples subjected to scCO$_2$ treatments.

TABLE 7

Supercritical CO$_2$ Treatments - Material Removed and Specific Surface Area

| Sample | Description | Duration | Material Removed from Drying | Material Removed from scCO2 | Material Removed from Heat | Total Material Removed | Surface Area (m2/g) | Correlation (R2) |
|---|---|---|---|---|---|---|---|---|
| 150420-01 | scCO2 - Condition 1 | 5 hour treatment 2 hour drying | Neglible | Neglible | N/A | Neglible | 54.248 | 0.99978 |
| 150420-01 | scCO2 - Condition 1 | 5 hour treatment 24 hour drying | Neglible | Neglible | N/A | Neglible | 37.578 | 0.99988 |
| 150420-01 | scCO2 Condition 1 | 5 hour treatment 24 hour drying 300 C. for 48 hours (44 hour ramp, 4 hour hold) | 79.24% | Neglible | 24.81% | Neglible | 51.721 | 0.99995 |
| 150604-01 | scCO2 - Condition 1 | 5 hour treatment 2 hour drying | Neglible | Neglible | N/A | Neglible | Inconclusive | Inconclusive |
| 150420-01 | scCO2 - Condition 2 | 5 hour treatment 2 hour drying | Neglible | Neglible | N/A | Neglible | 17.984 | 0.99994 |
| 150604-01 | scCO2 - Condition 2 | 5 hour treatment 2 hour drying | Neglible | Neglible | N/A | Neglible | 10.151 | 0.99988 |
| 150829-01 | scCO2 - Condition 3 | 18 hour treatment 2 hour drying | 79.24% | Neglible | N/A | 79.24% | 32.862 | 0.99991 |
| 150829-01 | scCO2 - Condition 3 | 18 hour treatment 2 hour drying 300 C. for 48 hours (44 hour ramp, 4 hour hold) | 79.24% | Neglible | 32.22% | 85.93% | 68.898 | 0.99994 |

Table 8 contains the percent material removed and averaged specific surface areas for the samples immersed in 30 and 35% hydrogen peroxide.

TABLE 8

Hydrogen Peroxide - Material Removed and Specific Surface Area

| Sample | Description | Duration | Material Removed from Drying | Material Removed from Peroxide | Material Removed from Heat | Total Material Removed | Surface Area (m²/g) | Correlation (R²) |
|---|---|---|---|---|---|---|---|---|
| 150829-01 | 30% peroxide soak | 24 hour drying at 105° C. | 79.24% | Not measured | N/A | ≥79.24% | 28.597 | 0.99915 |
| 150829-01 | 30% peroxide soak | 300 C. for 48 hours (44 hour ramp, 4 hour hold) | 79.24% | Not measured | 15.79% | ≥82.52% | 99.878 | 0.99962 |
| 150829-01 | 35% peroxide soak | 24 hour drying at 105° C. | 79.24% | 25.92% | N/A | ≥84.62 | 45.229 | 0.99998 |
| 150829-01 | 35% Peroxide Soak | 300 C. for 24 hours (20 hour ramp, 4 hour hold) | 79.24% | 25.92% | 17.87% | 87.37% | 91.958 | 0.99984 |
| 150829-01 | 35% Peroxide Soak | 300 C. for 48 hours (44 hour ramp, 4 hour hold) | 79.24% | 25.92% | 7.54% | 85.78% | 83.614 | 0.99992 |
| 150829-01 | 35% Peroxide Soak | 400 C. for 24 hours (20 hour ramp, 4 hour hold) | 79.24% | 25.92% | 34.19% | 89.88% | 94.339 | 0.99975 |
| 150829-01 | 35% Peroxide Soak | 400 C. for 48 hours (44 hour ramp, 4 hour hold) | 79.24% | 25.92% | 24.68% | 88.42% | 68.058 | 0.99971 |

Table 9 contains the percent material removed and averaged specific surface areas for the samples immersed in 35% hydrogen peroxide followed by UV treatment for 16 hours.

TABLE 9

Hydrogen Peroxide and UV Combination Treatment - Material Removed and Specific Surface Area

| Sample | Description | Duration | Material Removed from Drying | Material Removed from Peroxide | Material Removed from UV | Material Removed from Heat | Total Material Removed | Surface Area (m²/g) | Correlation (R²) |
|---|---|---|---|---|---|---|---|---|---|
| 150829-01 | 35% Peroxide Soak UV for 16 hours | 24 hour drying at 105°C. | 79.24% | 25.92% | Negligible | N/A | 84.62% | 68.246 | 0.99985 |
| 150829-01 | 35% Peroxide Soak UV for 16 hours | 300 C. for 24 hours (20 hour ramp, 4 hour hold) | 79.24% | 25.92% | Negligible | 15.08% | 86.94% | 92.569 | 0.99984 |
| 150829-01 | 35% Peroxide Soak UV for 16 hours | 300 C. for 48 hours (44 hour ramp, 4 hour hold) | 79.24% | 25.92% | Negligible | 2.48% | 85.00% | 94.523 | 0.99991 |
| 150829-01 | 35% Peroxide Soak | 400 C. for 24 hours (20 hour | 79.24% | 25.92% | Negligible | 35.28% | 90.05% | 85.564 | 0.99984 |

TABLE 9-continued

Hydrogen Peroxide and UV Combination Treatment - Material Removed and Specific Surface Area

| Sample | Description | Duration | Material Removed from Drying | Material Removed from Peroxide | Material Removed from UV | Material Removed from Heat | Total Material Removed | Surface Area (m²/g) | Correlation (R²) |
|---|---|---|---|---|---|---|---|---|---|
| | UV for 16 hours | ramp, 4 hour hold) | | | | | | | |

Discussion

Percent material removed typically increased with increasing temperature, with the highest difference witnessed between 200° C. and 300° C. with minimal changes between 400° C. and 500° C.

Small increases were observed in percent weight removed when heating for 7 days as compared to 5 days at 200° C. and 300° C. while changes were minimal for 400° C. and 500° C. conditions.

For 150420-01 and 150604-01 samples, specific surface area increased with increasing temperature and heat time until 400° C. was reached. An insignificant reduction in specific surface area was exhibited for a majority of samples heated at 400° C. as compared to 300° C. and a reduction >80% in specific surface area was measured at 500° C. as compared to samples heated at 400° C.

Greater material removal was typically achieved using the NovaScan UV Chamber while higher surface areas were achieved for samples processed at Opsytec.

Condition 1 for sample 150420-01 had the highest surface area with minimal surface area increases for other conditions/samples. Material removal was not included since the amount removed was negligible (<5%) and difficult to accurately determine for each sample.

Figure 8:
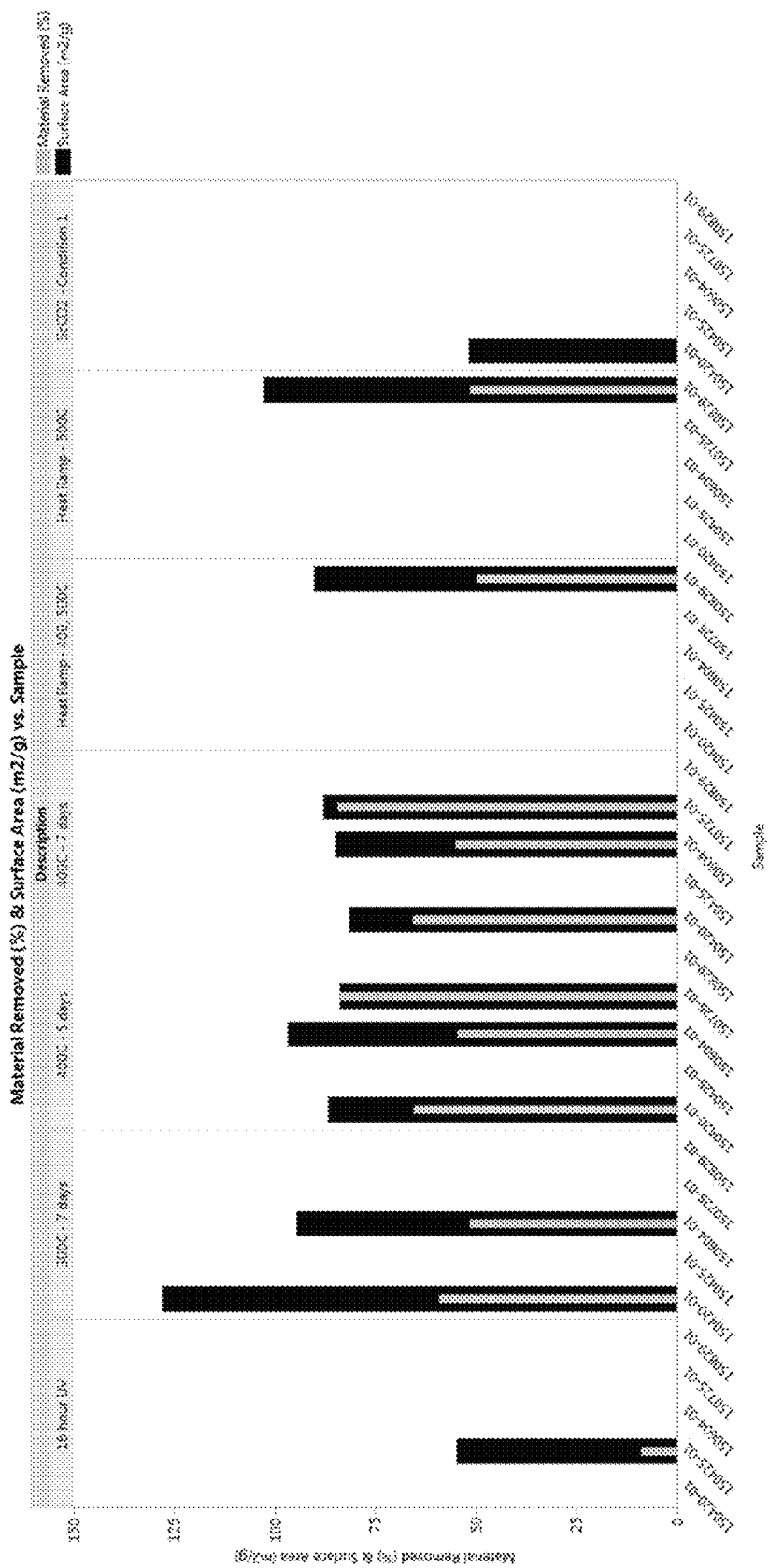
FIG. 8 highlights the samples with the highest specific surface areas from the various conditions investigated; the percentages of material removed for each sample are also displayed.

The samples displayed in FIG. 8 were selected since these samples had the highest surface areas from the various treatment conditions.

Solgel-derived 45S and 45S5 glass-ceramic samples containing sodium silicate, calcium lactate, and lactic acid were subjected to various heating temperatures for extended periods, heat ramp cycles, UV, and scCO2 to investigate changes in percent material removed and specific surface area. Subjecting the sample to UV for 16 hours followed by 400° C. for 36 hours resulted in maximized surface area and heating to 400° C. resulted in maximized material removal without excessively adversely affecting the pore structure. Sample treatment at 500° C. demonstrated insignificant changes in material removed while collapsing the pore structure with >80% reduction in specific surface area for all samples. Performing a slow heat ramp to 500° C. prevented pore collapse and resulted in samples with surface areas 80-90 m2/g; surface areas >100 m²/g for slow heat ramps to 300° C. UV samples processed by Opsytec for 16 hours exhibited surface areas >50 m²/g while samples processed internally with the NovaScan UV Chamber exhibited surface areas up to 20 m²/g depending on the sample. The scCO2 sample (150420-01, Condition 1) with the highest surface area exhibited ~50 m²/g. Treating a sample with 30% peroxide followed by a heat treatment at 300° C. for 48 hours resulted in a surface area of ~99.9 m²/g.

While the 400° C. samples display the highest amount of material removed, these samples were not dried before processing, accounting for a lower amount of material removed for the 500° C. heat ramp samples.

For all samples subjected to prolonged heat treatment, surface area increased when heating up to 300° C. but slight decreases were seen at 400° C. and sharp decreases were seen at 500° C.; performing a slow heat ramp to 500° C. appears to have resolved this issue since the 400° C. heat treatment and 500° C. heat ramp samples have comparable surface areas.

While the scCO$_2$ and UV treated samples possessed lower surface areas, these samples exhibited less discoloration after processing. Heat treatment samples were gray/black after treatment while the scCO$_2$ and UV treated samples were white/yellow after treatment. Samples treated with 30 and 35% hydrogen peroxide were white following treatment.

These results demonstrate that these treatment processes produce solgel-derived 45S5 and 45S glass-ceramics with higher surface areas than melt-derived 45S5 glass-ceramic for most conditions. Surface area was maximized with heat treatment at 300° C. for 7 days with a room temperature air dried sample provided the optimal conditions. Maximizing material removed while maintaining a high surface area can be achieved with heating to 400° C. or slowly ramping the heat to 500° C.

Example 3

Solgel-derived bioactive glass-ceramic samples were dried for 24 hours and then a slow ramp heated to 500° C. was initiated (23 hour ramp, 1 hour hold at 500° C.). The results are below:

TABLE 10

| Sample | Temperature (° C.) | Duration (hours) | Moisture Removed from Drying at 105 C. | Material Removed from Heat | Total Material Removed |
|---|---|---|---|---|---|
| 150725-01 | 105, 500 | 24, 24 | 66.28% | 52.61% | 84.02% |
| 150829-01 | 105, 500 | 24, 24 | 79.24% | 51.40% | 89.91% |

The percent material removed was determined in reference to the new weight following the 24 hour drying cycle.

Instead of the normal black coloration, the samples were gray.

Although the present invention has been described in considerable detail with reference to certain embodiments thereof, other embodiments are possible without departing from the present invention. The spirit and scope of the appended claims should not be limited, therefore, to the description of the preferred embodiments contained herein.

All embodiments that come within the meaning of the claims, either literally or by equivalence, are intended to be embraced therein.

Furthermore, the advantages described above are not necessarily the only advantages of the invention, and it is not necessarily expected that all of the described advantages will be achieved with every embodiment of the invention.

The invention claimed is:

1. A method for treating a solgel-derived bioactive glass-ceramic to remove organic residuals and/or impurities from the solgel-derived bioactive glass-ceramic, comprising:
    applying to the solgel-derived bioactive glass-ceramic at least one treatment after the solgel-derived bioactive glass-ceramic has undergone aging and drying steps of a solgel method, the at least one treatment is selected from:
    (i) a low temperature heat treatment comprising heating the solgel-derived bioactive glass-ceramic to a treatment temperature at or below 550° C. and holding the treatment temperature for the remainder of a heat treatment period;
    (ii) a stepwise low temperature heat treatment comprising stepwise heating the solgel-derived bioactive glass-ceramic to at least a first treatment temperature at or below about 550° C.;
    (iii) an ultraviolet (UV) light treatment;
    (iv) a supercritical carbon dioxide (scCO$_2$) treatment;
    (v) freeze drying or lyophilization; or
    (vi) an oxidation process;
    wherein the at least one treatment (i) through (vi) results in the removal of at least 5% of organic residuals and/or impurities from the solgel-derived bioactive glass-ceramic, while maintaining the pore structure of the solgel-derived bioactive glass-ceramic; and
    wherein any combination of treatments (i) through (vi) results in a synergistic removal of organic residuals and/or impurities from the solgel-derived bioactive glass-ceramic;
    wherein the solgel-derived bioactive glass-ceramic comprises 45% SiO$_2$, 6% P$_2$O$_5$, 24.5% CaO, and 24.5% Na$_2$O; and
    wherein the at least one treatment (i) through (vi) is for a time period of from about 5 to about 7 days or longer.

2. The method of claim 1, wherein the at least one treatment results in the removal of at least 10% of organic residuals and/or impurities from the solgel-derived bioactive glass-ceramic.

3. The method of claim 1, wherein the at least one treatment results in the removal of at least 20% of organic residuals and/or impurities from the solgel-derived bioactive glass-ceramic.

4. The method of claim 1, wherein the at least one treatment results in the removal of at least 50% of organic residuals and/or impurities from the solgel-derived bioactive glass-ceramic.

5. The method of claim 1, wherein the at least one treatment results in the removal of at least 75% of organic residuals and/or impurities from the solgel-derived bioactive glass-ceramic.

6. The method of claim 1, wherein the at least one treatment results in the removal of at least 90% of organic residuals and/or impurities from the solgel-derived bioactive glass-ceramic.

7. The method of claim 1, wherein the at least one treatment results in the removal of at least 99.9% of organic residuals and/or impurities from the solgel-derived bioactive glass-ceramic.

8. The method of claim 1, wherein the step (i) comprises applying at least two of the following treatments, wherein the step (i) is for a total treatment period of from about 5 to about 7 days or longer:
    20 hour ramp from 25° C. to 300° C., 4 hour hold at 300° C., wherein the total heating time is 24 hours;
    32 hour ramp from 25° C. to 300° C., 4 hour hold at 300° C., wherein the total heating time of 36 hours;
    44 hour ramp from 25° C. to 300° C., 4 hour hold at 300° C., wherein the total heating time of 48 hours;
    68 hour ramp from 25° C. to 300° C., 4 hour hold at 300° C., wherein the total heating time of 72 hours;
    24 hour ramp from 25° C. to 300° C., I hour hold at 300° C., wherein the total heating time of 25 hours;
    20 hour ramp from 25° C. to 400° C., 4 hour hold at 400° C., wherein the total heating time is 24 hours;
    32 hour ramp from 25° C. to 400° C., 4 hour hold at 400° C., wherein the total heating time of 36 hours;
    44 hour ramp from 25° C. to 400° C., 4 hour hold at 400° C., wherein the total heating time of 48 hours;
    68 hour ramp from 25° C. to 400° C., 4 hour hold at 400° C., wherein the total heating time of 72 hours;
    24 hour ramp from 25° C. to 400° C., I hour hold at 400° C., wherein the total heating time of 25 hours;
    20 hour ramp from 25° C. to 500° C., 4 hour hold at 500° C., wherein the total heating time is 24 hours;
    32 hour ramp from 25° C. to 500° C., 4 hour hold at 500° C., wherein the total heating time of 36 hours;
    44 hour ramp from 25° C. to 500° C., 4 hour hold at 500° C., wherein the total heating time of 48 hours;
    68 hour ramp from 25° C. to 500° C., 4 hour hold at 500° C., wherein the total heating time of 72 hours; or
    24 hour ramp from 25° C. to 500° C., I hour hold at 500° C., wherein the total heating time of 25 hours.

9. The method of claim 1, wherein the step (i) comprises heating the solgel-derived bioactive glass-ceramic to the treatment temperature between about 105° C. and at or below about 550° C.

10. The method of claim 1, wherein the step (ii) comprises applying at least two of the following treatments, wherein the step (ii) is for a total treatment period of from about 5 to about 7 days or longer:
    24 hour ramp from 25° C. to 400° C., 10 hour hold at 400° C., 10 hour ramp from 400° C. to 500° C., I hour hold at 500° C. (total heating time of 45 hours);
    5 hour ramp from 25° C. to 400° C., 5 hour hold at 400° C., 5 hour ramp from 400° C. to 500° C., 5 hour hold at 500° C. (total heating time of 20 hours);
    10 hour ramp from 25° C. to 400° C., 10 hour hold at 400° C., 10 hour ramp from 400° C. to 500° C., 10 hour hold at 500° C. (total heating time of 40 hours);
    15 hour ramp from 25° C. to 400° C., 15 hour hold at 400° C., 15 hour ramp from 400° C. to 500° C., 15 hour hold at 500° C. (total heating time of 60 hours);
    20 hour ramp from 25° C. to 400° C., 20 hour hold at 400° C., 20 hour ramp from 400° C. to 500° C., 20 hour hold at 500° C. (total heating time of 80 hours);
    5 hour ramp from 25° C. to 200° C., 5 hour hold, 5 hour ramp to 300° C., 5 hour hold, 5 hour ramp to 400° C., 5 hour hold (total heating time of 30 hours);
    5 hour ramp from 25° C. to 200° C., 5 hour hold, 5 hour ramp to 300° C., 5 hour hold, 5 hour ramp to 400° C., 5 hour hold, 5 hour ramp to 500° C., 5 hour hold (total heating time of 40 hours);
    10 hour ramp from 25° C. to 200° C., 10 hour hold, 10 hour ramp to 300° C., 10 hour hold, 10 hour ramp to 400° C., 10 hour hold, 10 hour ramp to 500° C., 10 hour hold (total heating time of 80 hours);

15 hour ramp from 25° C. to 200° C., 15 hour hold, 15 hour ramp to 300° C., 15 hour hold, 15 hour ramp to 400° C., 15 hour hold, 15 hour ramp to 500° C., 15 hour hold (total heating time of 120 hours); or 20 hour ramp from 25° C. to 200° C., 20 hour hold, 20 hour ramp to 300° C., 20 hour hold, 20 hour ramp to 400° C., 20 hour hold, 20 hour ramp to 500° C., 20 hour hold (total heating time of 160 hours).

11. The method of claim 1, wherein the step (i) comprises applying at least one of the following treatments:
rapid heating between 105° C. and ≤550° C.; or
rapid heating between 300° C. and 400° C.

12. The method of claim 1, wherein the step (ii) comprises applying at least one of the following treatments:
15 hour ramp from 25° C. to 200° C., 15 hour hold, 15 hour ramp to 300° C., 15 hour hold, 15 hour ramp to 400° C., 15 hour hold, 15 hour ramp to 500° C., 15 hour hold (total heating time of 120 hours); or 20 hour ramp from 25° C. to 200° C., 20 hour hold, 20 hour ramp to 300° C., 20 hour hold, 20 hour ramp to 400° C., 20 hour hold, 20 hour ramp to 500° C., 20 hour hold (total heating time of 160 hours).

\* \* \* \* \*